(12) United States Patent
Hawiger et al.

(10) Patent No.: US 9,370,549 B2
(45) Date of Patent: *Jun. 21, 2016

(54) COMPOSITIONS AND METHODS FOR TREATING AND PREVENTING HYPERLIPIDEMIA, FATTY LIVER, ATHEROSCLEROSIS AND OTHER DISORDERS ASSOCIATED WITH METABOLIC SYNDROME

(71) Applicant: Vanderbilt University, Nashville, TN (US)

(72) Inventors: Jack J. Hawiger, Nashville, TN (US); Ruth Ann Veach, Brentwood, TN (US); Jozef Zienkiewicz, Nashville, TN (US); Yan Liu, Nashville, TN (US); Robert D. Collins, Nashville, TN (US); Amy S. Major, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/705,121

(22) Filed: May 6, 2015

(65) Prior Publication Data

US 2015/0250850 A1    Sep. 10, 2015

Related U.S. Application Data

(63) Continuation of application No. 14/349,918, filed as application No. PCT/US2012/058982 on Oct. 5, 2012, now Pat. No. 9,044,433.

(60) Provisional application No. 61/544,105, filed on Oct. 6, 2011.

(51) Int. Cl.
| | |
|---|---|
| *A61K 38/16* | (2006.01) |
| *A61K 38/12* | (2006.01) |
| *A61K 38/08* | (2006.01) |
| *A61K 31/397* | (2006.01) |
| *A61K 45/06* | (2006.01) |

(52) U.S. Cl.
CPC .............. *A61K 38/16* (2013.01); *A61K 31/397* (2013.01); *A61K 38/08* (2013.01); *A61K 38/12* (2013.01); *A61K 45/06* (2013.01)

(58) Field of Classification Search
None
See application file for complete search history.

(56) References Cited

U.S. PATENT DOCUMENTS

| 6,624,146 B1 | 9/2003 | Imamura et al. | |
|---|---|---|---|
| 7,553,929 B2 * | 6/2009 | Hawiger | A61K 38/1709 530/317 |
| 9,044,433 B2 * | 6/2015 | Hawiger | A61K 38/12 |
| 2004/0235746 A1 | 11/2004 | Hawiger et al. | |

FOREIGN PATENT DOCUMENTS

| WO | 0137821 | 5/2001 |
|---|---|---|
| WO | 2009039966 | 4/2009 |

OTHER PUBLICATIONS

Moore et al.: "In Viro Islet Protection by a Nuclear Import Inhibitor in a Mouse Model of Type 1 Diabetes", PLoS One p. 1-12, vol. 5, Issue 10, e13235, Oct. 2010.
Hui et al.: "The inhibitory effect of polypeptide cSN50 on alcoholic hepatic injuries through blocking the binding of NF-kappa B to importin alpha", Scandinavian Journal of Gastroenterology, (Jul. 1, 2011) 46(7-8): 931-940.
Dabek et al.: "Nuclear factor kappa-light-chain-enhancer of activated B cells (NF-κB): A new potential therapeutic target in atherosclerosis?", Pharmacological Reports (Sep. 1, 2010) 62(5): 778-783.
Han et al.: "Reciprocal and coordinate regulation of serum amyloid A versus apolipoprotein A-I and paraoaonase-1 by inflammation in murine hepatocytes", Arteriosclerosis, Thrombosis, and Vascular Biology (Aug. 1, 2006) 26(8): 1806-1813.
Lin et al.: "Inhibition of nuclear translocation of transcription factor NE-KB by a synthetic peptide containing a cell membrane-permeable motif and nuclear localization sequence", Journal of Biological Chemistry (Jun. 16, 1995) 270(24): 14255-14258.
Extended European Search Report completed on Mar. 18, 2015 in EP Application No. 12838976.4 (17 pages).

* cited by examiner

*Primary Examiner* — Christina Bradley
(74) *Attorney, Agent, or Firm* — Meunier Carlin & Curfman LLC

(57) ABSTRACT

The present invention relates to compositions and methods for treating diseases associated with dyslipidemia, including hypercholesterolemia, hypertriglyceridemia, steatohepatitis, atherosclerosis, obesity, hyperglycemia, metabolic syndrome, and related aspects of and conditions associated with metabolic syndrome. The compositions and methods disclosed herein are useful for regulating the lipid balance (lipid homeostasis) in a subject. Compositions and methods including a Nuclear Transport Modifier may be administered to a subject to modulate the transport of transcription factors, mediated by nuclear import adaptors, into the nucleus of a cell resulting in a decrease in cholesterol and triglyceride levels in the blood and liver, a decrease in atherosclerotic lesion size, a decrease in body weight and in hyperglycemia, a reduction of fatty liver inflammation, and an improvement in liver function.

18 Claims, 11 Drawing Sheets

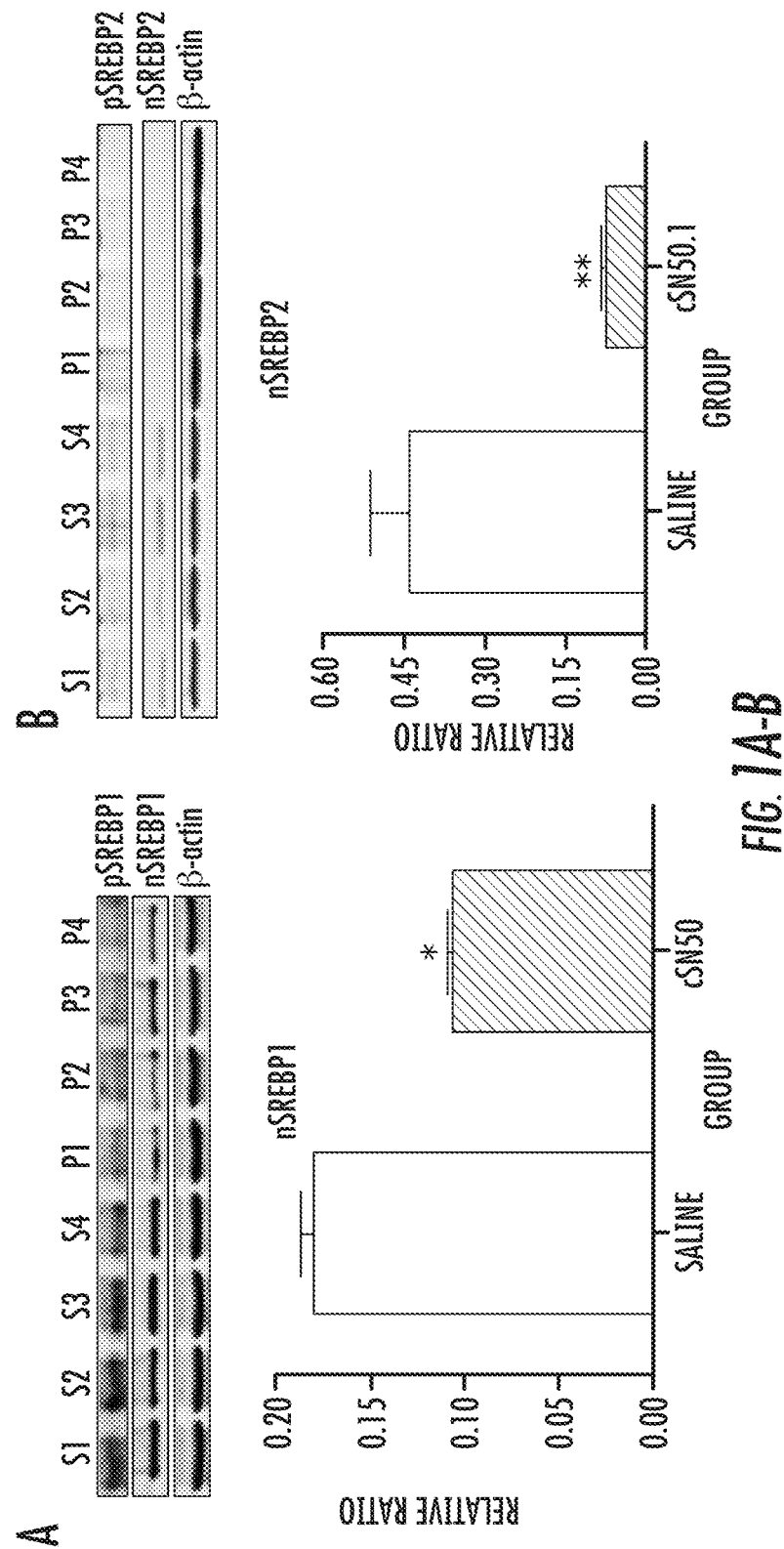
FIG. 1A-B

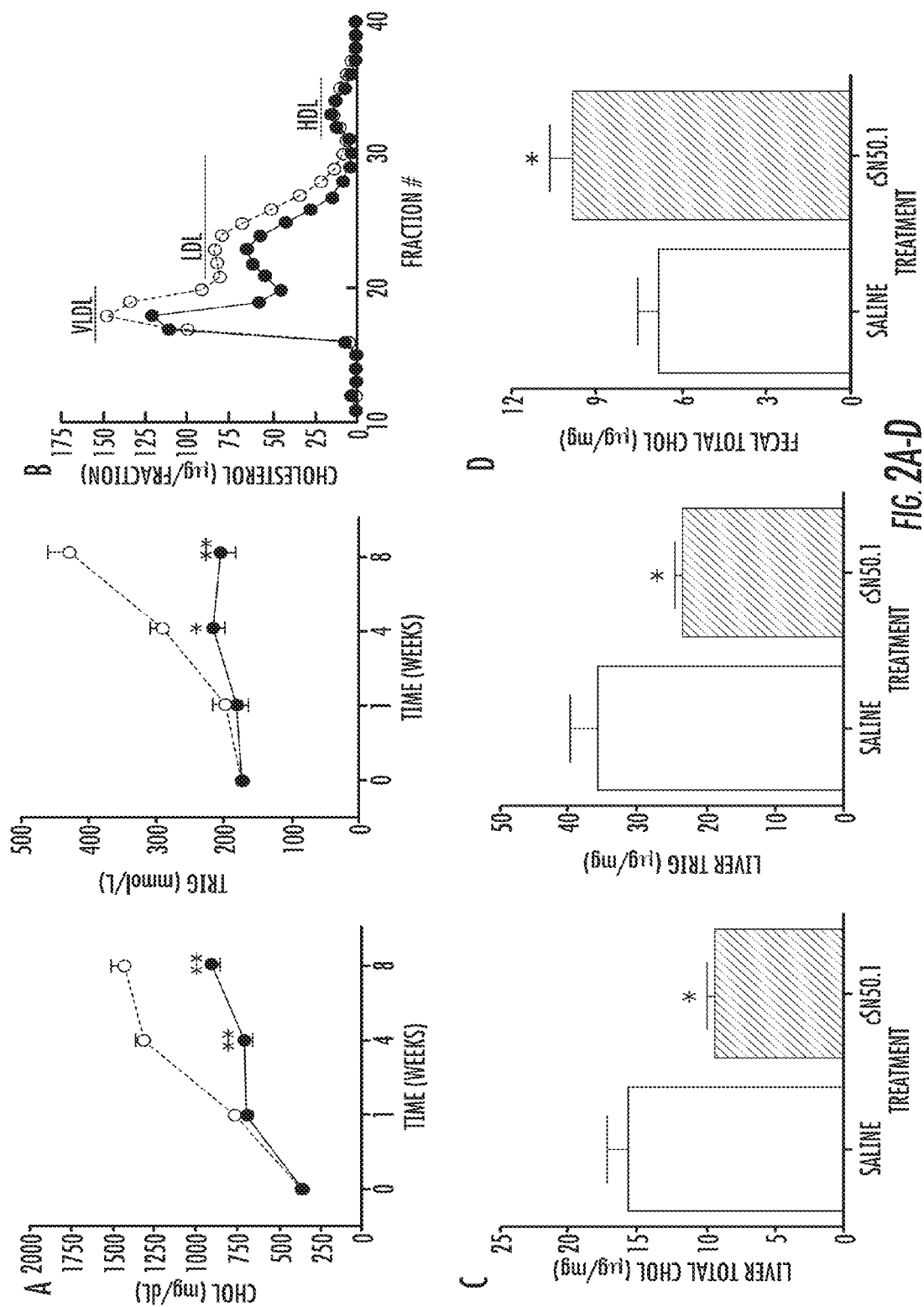
FIG. 2A-D

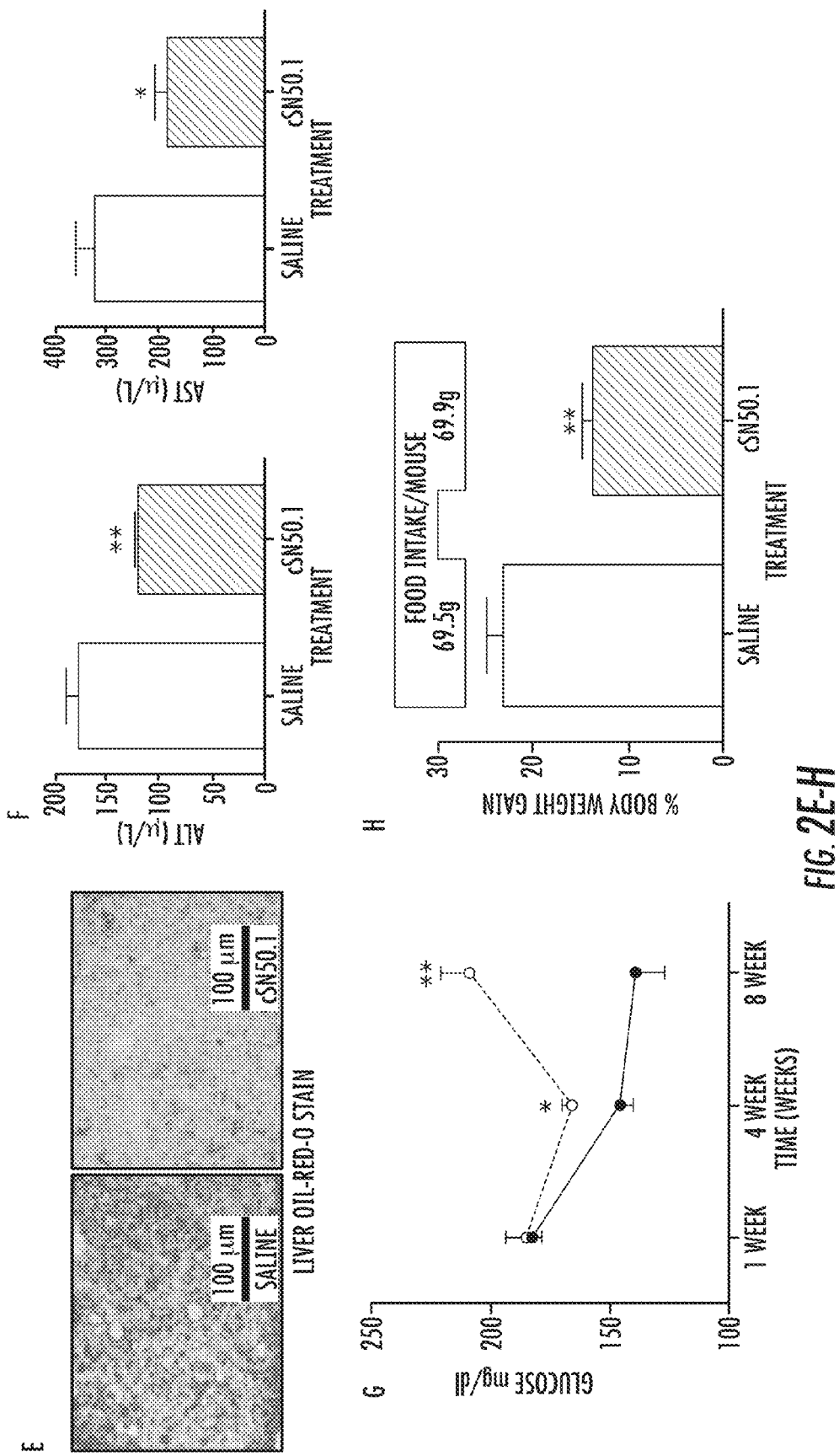
FIG. 2E-H

COMPOSITIONS AND METHODS FOR TREATING AND PREVENTING HYPERLIPIDEMIA, FATTY LIVER, ATHEROSCLEROSIS AND OTHER DISORDERS ASSOCIATED WITH METABOLIC SYNDROME

CROSS REFERENCE TO RELATED APPLICATIONS

This application is a continuation application of U.S. nonprovisional application Ser. No. 14/349,918, filed Apr. 4, 2014, which is a 371 U.S. national stage entry of International application no. PCT/US2012/058982, filed Oct. 5, 2012, which claims priority to U.S. provisional application No. 61/544,105, filed Oct. 6, 2011, all of which are incorporated herein by reference in their entireties.

STATEMENT REGARDING FEDERALLY SPONSORED RESEARCH OR DEVELOPMENT

This invention was made with government support under Grant Nos. HL085833, AA015752, HL088364, HL089310, and 1KO8DK090146 awarded by the National Institutes of Health. The U.S. government has certain rights in the invention.

FIELD

The invention relates generally to the fields of biochemistry, cell biology, molecular genetics, endocrinology, and cardiovascular medicine.

BACKGROUND

Contemporary Western type diets challenge lipid and glucose homeostasis by overloading blood with cholesterol, triglycerides, and glucose. Their excess has serious consequences for the cardiovascular system (atherosclerosis) and liver (steatohepatitis), and contributes to the metabolic syndrome, a leading cause of mortality worldwide. Disordered lipid and glucose metabolism elicits an inflammatory response (metabolic inflammation) by signaling to the nucleus through the nuclear transport of stress-responsive transcription factors (SRTFs). They reprogram immune and non-immune cells into an inflammatory phenotype. Lipid homeostasis comprises a tightly regulated physiologic balance between dietary lipid intake, endogenous production, and intestinal disposal. Derangement of lipid homeostasis is linked to excessive signaling to the nucleus by sterol regulatory element-binding proteins (SREBPs) 1a, 1c, and 2 (Horton, J. D., Goldstein, J. L., and Brown, M. S. (2002) J Clin Invest 109, 1125-11314-8); Ferre, P., and Foufelle, F. (2007) Horm Res 68, 72-82; Raghow, R., Yellaturu, C., Deng, X., Park, E. A., and Elam, M. B. (2008) Trends Endocrin Met 19, 65-73; Jeon, T. I., and Osborne, T. F. (2012) Trends Endocrin Met 23, 65-72). SREBPs are transcription factors with a basic helix-loop helix leucine zipper (bHLH-Zip) domain. They are sequestered in the membrane of the endoplasmic reticulum (ER) in a complex with the sterol sensor and transporter SREBP cleavage-activating protein (Scap), which regulates their subsequent transit from the ER to the Golgi apparatus. There, two membrane proteases process SREBPs to release a ~60 kDa NH2-terminal segment termed nuclear SREBP (nSREBP), that contains the bHLH-Zip region. As nSREBPs lack a classic nuclear localization sequence (NLS), their shuttling to the nucleus is provided solely by a unique association with importin beta rather than first being complexed with one of the importins/karyopherins alpha that utilize importin beta for docking to the nuclear pore (Lee, S. J., Sekimoto, T., Yamashita, E., Nagoshi, E., Nakagawa, A., Imamoto, N., Yoshimura, M., Sakai, H., Chong, K. T., Tsukihara, T., and Yoneda, Y. (2003)). Science 302, 1571-15759). Importin beta-mediated nuclear translocation of SREBPs culminates in activation of a set of genes that encode proteins involved in synthesis of cholesterol and its cellular binding pathways and in fatty acid, triglyceride, and phospholipid synthetic pathways (Horton, J. D., Goldstein, J. L., and Brown, M. S. (2002) J Clin Invest 109, 1125-11314-8). Moreover, carbohydrate response element binding protein (ChREBP) is a glucose-activated transcription factor involved in the development of metabolic syndrome (Iizuka, K., and Horikawa, Y. (2008) Endocrine journal 55, 617-624). ChREBP belongs to the same bHLH-Zip family as SREBPs and in response to elevated blood glucose regulates expression of genes involved in glycolysis, lipogenesis, and gluconeogenesis that convert excess carbohydrates into liver triglycerides rather than glycogen. Though ChREBP is a bHLH-Zip domain transcription factor in the same family as SREBPs, it also contains a classic NLS recognized by importins alpha (Ge, Q., Nakagawa, T., Wynn, R. M., Chook, Y. M., Miller, B. C., and Uyeda, K. (2011) J Biol Chem 286, 28119-28127).

The autoregulatory loop of cholesterol and fatty acid synthesis is disrupted by genetic defects in LDL receptor (LDLR) function that increase the risk of early heart attack by more than 10-fold in heterozygous familial hypercholesterolemia. Compounding hyperlipidemia, the inflammatory response enhances atherosclerosis development. This process depends on the prominent role of macrophages as well as T and B lymphocytes, and other cells of the immune system. Overabundant cholesterol-carrying low-density lipoproteins that saturate the blood vessel wall at zones of hemodynamic stress and formation of cholesterol crystals evoke an inflammatory response mediated by the NLRP3 inflammasome, generating mature proinflammatory cytokines interleukin-1β (IL-1β) and interleukin 18 (IL-18).

These and many other mediators that participate in the atherosclerosis-promoting inflammatory process are regulated by nuclear factor-kappa B (NF-κB) and other SRTFs, such as AP-1, NFAT, and STAT1. SRTFs are widely distributed in the vascular and immune cells that gather in atherosclerotic lesions (Hansson, G. K. & Hermansson, A., Nat Immunol 12 (3), 204-212 (2011); Brand, K. et al., J. Clin. Invest. 97 (7), 1715-1722 (1996)). SRTFs are transported to the nucleus in response to proinflammatory stimuli, including Western type diet-induced hyperlipidemia, recognized by innate immunity Toll-like receptors, adaptive immunity T and B cell antigen receptors, and cytokine receptors. In the nucleus, SRTFs activate genes that encode mediators of inflammation. Autoimmune responses to LDL play a significant role in the development of atherosclerosis.

There is an urgent need for therapeutics that can arrest Western diet-type-driven hyperlipidemia, fatty liver, atherosclerosis, Type 2 diabetes, and obesity, and prevent complications associated with such disorders (e.g., several cardiovascular, hepatobiliary, and renal complications).

BRIEF SUMMARY

Hyperlipidemia, fatty liver, and, atherosclerosis, which are on a steady rise worldwide, were suppressed by the presently claimed compositions including a Nuclear Transport Modifier (NTM) in a mouse model of familial hypercholesterolemia without overt signs of general toxicity in the experiments described herein. As obesity is the most frequent cause of hepatic steatosis, a harbinger of cirrhosis and liver failure, the significant reduction in body weight gain while food intake was unchanged in NTM-treated mice is also important. Moreover, NTM treatment prevented fatty liver with elevated transaminases, a hallmark of steatohepatitis, which can lead to end-stage liver disease accounting for up to 14% of liver transplants in the US. These derangements in lipid and glucose homeostasis, causing liver and vascular inflammation, are corrected by NTM treatment. Thus, the experimental results described herein establish the nuclear transport adaptor, importin beta, as a new target for controlling aberrant lipid and carbohydrate metabolism that underlies hyperlipidemia, hyperglycemia, fatty liver, atherosclerosis, and their complications. Taken together, these findings support therapeutic compositions and methods involving the dual lipid-lowering and anti-inflammatory actions of NTM in correction of metabolic syndrome.

The present invention relates to compositions, methods, and kits for treating diseases associated with metabolic and vascular inflammation encompassing hypercholesterolemia, hypertriglyceridemia, steatohepatitis, atherosclerosis, obesity, hyperglycemia and other facets of metabolic syndrome. A composition including a NTM (e.g., cSN50.1), with or without an additional therapeutic agent such as a statin or ezetimibe, for example, may be administered to a subject for treatment and/or prevention of these disorders. The compositions, methods, and kits disclosed herein are useful for regulating the lipid balance (lipid homeostasis) in a subject. Methods including administering a NTM reduce the activity (e.g., binding) of nuclear transport adaptors thereby modulating transport of SRTFs such as NFκB, AP-1, NFAT, STAT1, SREBPs such as SREBP1a, SREBP1c, and SREBP2, as well as ChREBP into the nucleus. Administration of an NTM also downregulates gene expression of SREBPs and their target genes (e.g., HMG-CoA reductase (hmgcr), ATP citrate lyase (acly), fatty acid synthase-1 (fasn1)) and Niemann-Pick C1-like1 protein (npc1l1) in the liver.

A nuclear transport checkpoint mediated by importins alpha and beta is positioned downstream of immunoreceptors and MyD88 thereby serving as a common nexus in the innate and adaptive immunity pathways that signal to the nucleus (Hawiger, J. (2001) Immunologic research 23, 99-109). Thus, bifunctional NTM can attenuate importins alpha-mediated transport of SRTFs and importin beta-mediated transport of SREBPs and ChREBP. As SREBPs lack a classic NLS, their nuclear translocation is solely mediated by association of their bHLHZip region with importin beta. In contrast, proinflammatory SRTFs, exemplified by NF-κB, bear an NLS that forms a complex with one of the importins/karyopherins alpha that then utilize importin beta for docking to the nuclear pore (Hawiger, J. (2001) Immunologic research 23, 99-109). Our studies document that NTM displays a dual function, inhibition of nuclear transport of SREBPs with subsequent attenuation of their target genes responsible for hyperlipidemia and reduced nuclear transport of proinflammatory SRTFs exemplified by NFκB, which controls the inflammatory response.

Nuclear Transport Modifiers include but are not limited to cSN50.1, cSN50, cSN50.1 Beta and SN50. Uses of this technology include methods and compositions for treating or preventing diseases associated with hyperlipidemia, including hypercholesterolemia, hypertriglyceridemia, steatohepatitis, atherosclerosis, and metabolic syndrome. The compositions disclosed herein may be administered to a subject to decrease the levels of cholesterol and triglycerides in the plasma and liver. These compositions also increase the level of cholesterol that is disposed off by the body by preventing its intestinal uptake (absorption). In atherosclerosis-prone mice, the NTMs disclosed herein improve deranged lipid metabolism, improve liver function, avert atherosclerosis, and afford liver cytoprotection.

Unless otherwise defined, all technical terms used herein have the same meaning as commonly understood by one of ordinary skill in the art to which this invention belongs.

As used herein, the term "homeostasis" means a state of physiological equilibrium produced by a balance of functions and of chemical composition within an organism.

As used herein, the term "hyperlipidemia" means elevated concentrations of lipids in the blood. By the term "dyslipidemia" is meant abnormality in, or abnormal amounts of, lipids and lipoproteins in the blood.

As used herein, the term "atherosclerosis" means a slowly progressing chronic vascular inflammatory disorder affecting primarily large and medium-sized arteries and characterized by the accumulation of lipids, fibrous elements, and immune cells that comprise a plaque which contributes to narrowing of blood vessel and its occlusion upon formation of a thrombus.

As used herein, the terms "Nuclear Transport Modifier" and "NTM" mean a component that is capable of modulating (e.g., decreasing the activity or expression of) at least one nuclear transport adaptor (e.g., importin alpha, importin beta) and thus reducing the transport of factors, such as transcription factors and binding proteins, into the nucleus. These terms are used interchangeably with "inhibitor of nuclear import" and "nuclear import inhibitor."

As used herein, the phrases "nuclear import adaptor" and "nuclear transport adaptor" mean a cell component capable of mediating transport of a protein usually larger than 45 kD (e.g., a transcription factor) into the nucleus. An example of a nuclear transport adaptor is an importin also known as karyopherin.

As used herein, "protein" and "polypeptide" are used synonymously to mean any peptide-linked chain of amino acids, regardless of length or post-translational modification, e.g., glycosylation or phosphorylation.

By the term "gene" is meant a nucleic acid molecule that codes for a particular protein, or in certain cases, a functional or structural RNA molecule.

As used herein, a "nucleic acid" or a "nucleic acid molecule" means a chain of two or more nucleotides such as RNA (ribonucleic acid) and DNA (deoxyribonucleic acid).

The terms "patient," "subject" and "individual" are used interchangeably herein, and mean a subject (e.g., vertebrate, mammalian (such as human), reptilian, piscine, avian, etc.) to be treated, diagnosed and/or to obtain a biological sample from.

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and noncovalent (hydrogen bonding, hydrophobic, ionic, and van der Waals).

The term "labeled," with regard to a nucleic acid, protein, probe or antibody, is intended to encompass direct labeling of the nucleic acid, protein, probe or antibody by coupling (i.e., physically or chemically linking) a detectable substance (detectable agent) to the nucleic acid, protein, probe or antibody.

As used herein, the terms "therapeutic," and "therapeutic agent" are used interchangeably, and are meant to encompass any molecule, chemical entity, composition, drug, therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, cells, natural or synthetic compounds and the like.

As used herein, the term "treatment" is defined as the application or administration of a therapeutic agent to a patient or subject, or application or administration of the therapeutic agent to an isolated tissue or cell line from a patient or subject, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

Accordingly, described herein is a composition including a pharmaceutically acceptable carrier and an isolated peptide including the amino acid sequence set forth in SEQ ID NO:3 or the amino acid sequence set forth in SEQ ID NO:4 in an amount sufficient to reduce nuclear translocation of at least one SREBP or ChREBP and treat or prevent one or more of the following conditions: hyperlipidemia, fatty liver, steatohepatitis, atherosclerosis, obesity, hyperglycemia, metabolic syndrome, and a condition associated with metabolic syndrome. The composition may further include an additional therapeutic agent for treating or preventing the condition, such as an inhibitor of cholesterol synthesis (e.g., a statin). The at least one SREBP or ChREBP may be nuclear forms of SREBP1a, SREBP1c, SREBP2, and ChREBP.

Also described herein is a method of treating or preventing fatty liver or atherosclerosis in a mammalian subject (e.g., human). The method includes administering a composition including a NTM to the mammalian subject in an amount effective for reducing importin alpha-mediated nuclear translocation of at least one SRTF, reducing importin beta-mediated nuclear translocation of SREBPs and ChREBP, and reducing inflammation caused by metabolic dysregulation in the mammalian subject. The NTM may bind to importin alpha, to importin beta, or to both importin alpha and importin beta. The subject may have fatty liver or be predisposed to fatty liver, and in such an embodiment, the at least one SRTF can be NFκB, and the inflammation can be steatohepatitis. Administration of the composition may result in improved liver function, reduced accumulation of cholesterol and triglycerides, a reduction in body weight and normalization of elevated blood glucose levels. The subject may have atherosclerosis, and administration of the composition can result in a reduction of at least one atherosclerotic lesion in the subject, and in this embodiment, the at least one SRTF can be one or more of: NFκB, AP-1, NFAT and STAT1. Administration of the composition can prevent or reduce vascular inflammation associated with atherosclerosis. The NTM can be cSN50 having the sequence set forth in SEQ ID NO:2, cSN50.1 having the sequence set forth in SEQ ID NO:3, cSN50.1 Beta having the sequence set forth in SEQ ID NO:4, or a polypeptide including SSHR-2 having the sequence set forth in SEQ ID NO:10 and a solubility tag. The composition may be administered by any suitable route, including, for example, orally.

Further described herein is a method of treating a cardiovascular disease, metabolic disease, or liver disease associated with dyslipidemia, hyperglycemia and/or inflammation in a mammalian subject (e.g, a human). The method includes administering to the mammalian subject a composition including a NTM in an amount effective to reduce nuclear transport of at least one SREBP, reduce expression of the at least one SREBP, and reduce expression of at least one gene involved in cholesterol, triglyceride, glucose metabolism or fatty acid synthesis (e.g., HMG-CoA reductase (hmgcr), ATP citrate lyase (acly), fatty acid synthase-1 (fasn1), and Niemann-Pick C1-like1 Protein (npc1l1)). The cardiovascular disease, metabolic disease, or liver disease can be, for example, hyperlipidemia, fatty liver, atherosclerosis, hypercholesterolemia, obesity, metabolic syndrome or hyperglycemia. The at least one gene can be involved in glucose metabolism and can be a ChREBP-regulated gene that encodes a protein involved in at least one of: glycolysis, lipogenesis, and gluconeogenesis. In the method, expression of the at least one gene can be reduced in the subject's liver. The NTM can be, for example, cSN50 having the sequence set forth in SEQ ID NO:2, cSN50.1 having the sequence set forth in SEQ ID NO:3, SSHR-2 having the sequence set forth in SEQ ID NO:10, or cSN50.1beta having the sequence set forth SEQ ID NO:4. The composition can be administered by any suitable route, e.g., orally. The composition can further include an additional therapeutic agent for treating or preventing the cardiovascular disease, metabolic disease, or liver disease, such as an inhibitor of cholesterol synthesis (e.g., a statin), or an inhibitor of cholesterol uptake (e.g., ezetimibe and its congeners). The composition is administered in an amount sufficient to decrease plasma cholesterol concentration and/or plasma triglyceride concentration. The composition can be administered in an amount sufficient to decrease one or more of: concentration of cholesterol in the liver, concentration of triglycerides in the liver, and concentration of fatty acids in the liver. If the subject is suffering from atherosclerosis and has an atherosclerotic lesion, administration of the composition decreases the area of at least one atherosclerotic lesion and decreases vascular inflammation. Additionally, administration of the composition can decrease an elevated blood glucose concentration and decrease liver lipid content.

Although compositions, kits, and methods similar or equivalent to those described herein can be used in the practice or testing of the present invention, suitable compositions, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIGS. 1A-1C are a pair of immunoblots and a series of graphs showing that NTM treatment attenuates expression of the master regulators of lipid metabolism, SREBP transcription factors, and their target gene transcripts in ldlr$^{-/-}$ mice fed a Western diet. FIG. 1A, and FIG. 1B: Immunoblot analysis of SREBP1 (FIG. 1A) and SREBP2 (FIG. 1B) proteins in whole-cell liver extracts from mice treated with saline (S1-S4) or cSN50.1 peptide (P1-P4) for 8 weeks. Full-length precursor (pSREBP, apparent size ~125 kDa) and mature nuclear (nSREBP, apparent size ~68 kDa) forms are present in liver extracts from control mice but are suppressed in extracts from NTM-treated mice. Quantitative analysis of immunoblots indicates significant suppression of nSREBP1 and nSREBP2 expressed as their relative ratio to beta actin. FIG. 1C: Transcript expression of SREBP1 and SREBP2 and their target genes in the livers of mice treated for 4 and 8 weeks with saline (white bars) or cSN50.1 peptide (black bars). Expression levels were measured by real time RT-PCR with 18 S mRNA used as an invariant control. Shown are the mean+SEM of 5 mice per group (* denotes p<0.05,  denotes p<0.005 and * denotes p<0.0005 by Student's t test).

FIGS. 2A-2H are a series of graphs and photographs of histological sections showing that NTM reduces hyperlipidemia, fatty liver, hyperglycemia, and weight gain in ldlr$^{-/-}$ mice fed a Western diet (n≥5 mice/group). At indicated times, plasma concentrations of cholesterol, triglycerides and glucose were determined in mice fed a Western diet and treated with cSN50.1 peptide (0.7 mg/mouse) or saline thrice daily. After 8 weeks, liver cholesterol and triglyceride concentrations were measured as well as cholesterol content of feces, and plasma concentrations of ALT and AST. Histological sections of liver were analyzed for lipid content. FIGS. 2A, 2B, and 2G: saline=open circles, cSN50.1=solid circles. FIG. 2A: Plasma concentrations of cholesterol and triglycerides at 0, 1, 4, and 8 weeks. FIG. 2B: FPLC profile of plasma lipoproteins from ldlr$^{-/-}$ mice at 8 weeks. FIG. 2C: Liver concentrations of cholesterol and triglycerides at 8 weeks. FIG. 2D: Fecal cholesterol at 8 weeks. FIG. 2E: Liver sections stained with Oil-red-O for neutral lipids at 8 weeks. FIG. 2F: Liver transaminases ALT and AST in plasma at 8 weeks FIG. 2G: Glucose concentrations in plasma at 1, 4 and 8 weeks. FIG. 2H: Body weight gain (%) and food intake (g) after 4 weeks of Western diet (* denotes p<0.05,  denotes p<0.005 and * denotes p<0.0005 by Student's t test).

FIG. 3A: Six week old ldlr$^{-/-}$ mice (n=5 mice/group) were treated with 0.7 mg/mouse cSN50.1 for eight weeks twice daily (Group 1) or for either the first 4 weeks (Group 2) or last 4 weeks (Group 3). Control mice were given an equivalent volume of saline twice daily for the entire 8 weeks (Group 4). See treatment key above the graph in FIG. 3A. Average lesion area was determined by Oil-Red-O analysis of the aortic sinus (* denotes p<0.05 by Kruskal Wallis with a Dunnett's Multiple Comparison post-test). FIG. 3B: Oil-red-O sections of the aortic sinus following 8 weeks of treatment with cSN50.1 or saline. FIG. 3C: Six week old ldlr$^{-/-}$ mice were treated with saline (n=11) or cSN50.1 (n=17) delivered by osmotic pump for 4 weeks. (* denotes p<0.05 by Mann Whitney).

FIG. 4A: Nuclear translocation of transcription factors that bear a basic helix-loop-helix leucine zipper (bHLH) motif, such as the sterol regulatory element-binding proteins (SREBPs), is mediated by binding of their bHLH region directly to importin beta (imp β, left). Consequently, over 30 genes that encode proteins involved in cholesterol, triglyceride, and fatty acids synthesis are activated. Transcription factors containing a classic nuclear localization sequence (NLS) motif, such as nuclear factor kappa B (NFκB), are ferried by binding of their NLS region to importin alpha (imp α, right), which then form a complex with importin beta for nuclear translocation to activate a myriad of genes that encode mediators of inflammation and immunity. FIG. 4B: In cells treated with NTM peptide, the SSHR-2 domain of the peptide occupies the bHLH-Zip docking site on importin beta (left) while the NLS domain occupies the NLS binding pocket on importin alpha (right), preventing transcription factor attachment and subsequent nuclear translocation and gene transcription. Please note that nuclear translocation of the carbohydrate regulatory element-binding protein (ChREBP) that bears both bHLH-Zip and NLS motifs may be inhibited by NTM either by its binding to importin beta that recognizes the bHLH-Zip motif or to importin alpha that recognizes the NLS motif.

DETAILED DESCRIPTION

Figure 1C:
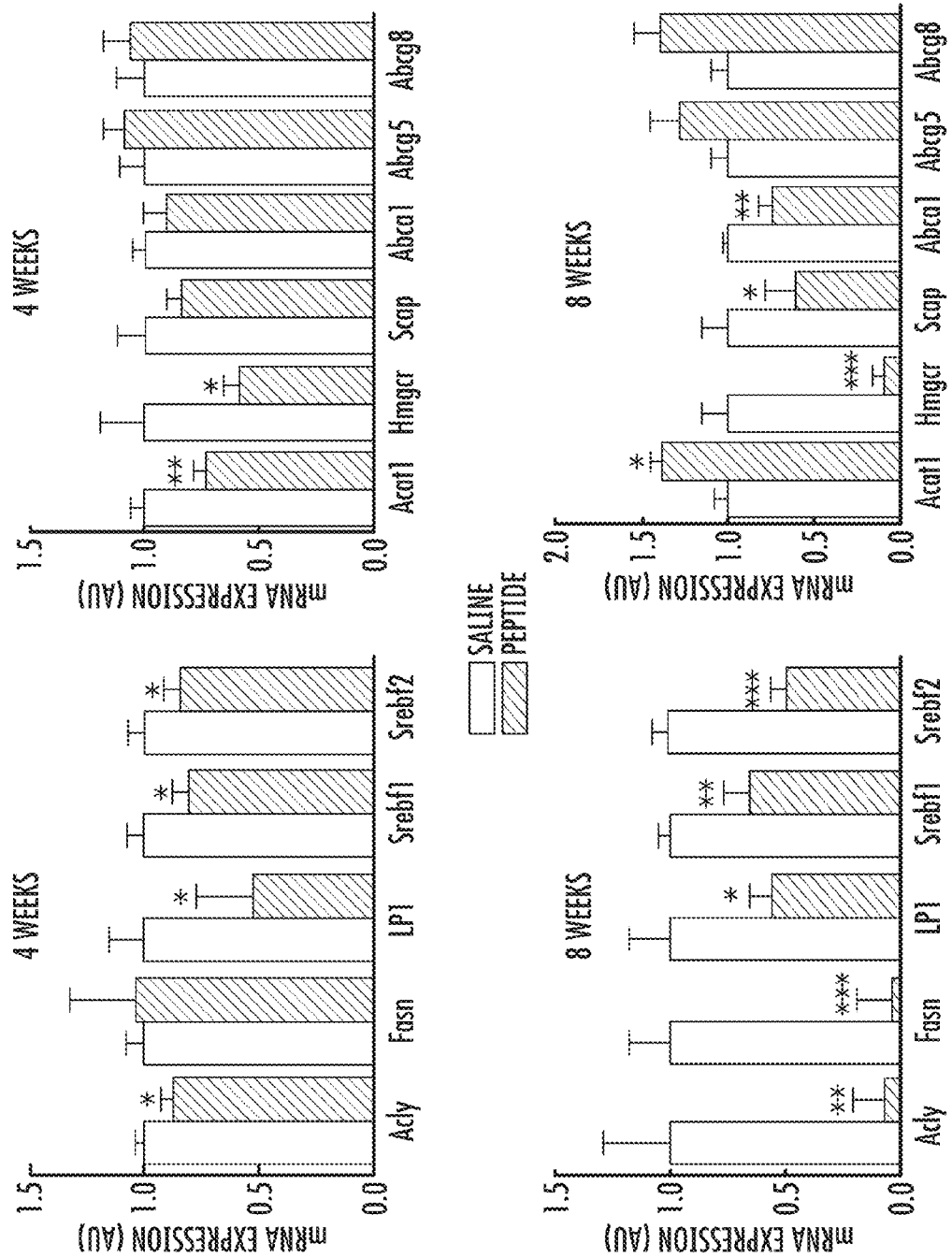

Described herein are compositions and methods for treating diseases associated with dyslipidemia and/or inflammation, including hypercholesterolemia, hypertriglyceridemia, fatty liver with steatohepatitis, atherosclerosis, hyperglycemia, obesity, and metabolic syndrome. Based on the experimental results described below, NTMs are able to decrease the levels of cholesterol and triglycerides in the plasma and liver, decrease fat content in the liver, increase intestinal disposal of cholesterol, promote weight loss, reduce inflammation (e.g., vascular inflammation) by decreasing atherosclerotic lesion size and attenuating fatty liver inflammation, and suppress the genomic program of cholesterol and fatty acid synthesis in the liver.

Nuclear Transport Modifiers (NTMs) target nuclear transport adaptors. Nuclear Transport Modifiers suppress signaling to the nucleus mediated by transcription factors that include but are not limited to NFκB, AP-1, NFAT, STAT1, SREBP1a, SREBP1c, and SREBP2, and ChREBP that utilize importins alpha and beta for nuclear transport. SRTFs such as NFκB, AP-1, NFAT, STAT1 are transported to the nucleus in response to proinflammatory stimuli. In the nucleus, SRTFs activate genes that encode mediators of inflammation (Hawiger, J., Immunol Res 23 (2-3), 99-109 (2001)). SREBPs such as SREBP1a, SREBP1c, and SREBP2, bind to the sterol regulatory element DNA sequence. When intracellular sterol levels are low, SREBPs are proteolytically cleaved and are transported to the nucleus. The binding of SREBPs to the sterol regulatory element DNA sequence upregulates the synthesis of enzymes involved in sterol biosynthesis such as HMGCo-A reductase and cholesterol binding proteins, such as Niemann-Pick C1-like1 protein.

Nuclear Transport Modifiers include but are not limited to cSN50, cSN50.1, cSN50.1 beta, and SN50. Any cell-penetrating peptide or peptidomimetic that is capable of modulating a nuclear transport adaptor and changing its ability to facilitate or enable entry of a transcription factor into the nucleus may be a Nuclear Transport Modifier.

SN50 is a fragment linked peptide combining the signal sequence hydrophobic region (SSHR) of the Kaposi fibroblast growth factor (K-FGF) and the nuclear localization signal (NLS) of the p50 subunit of NFκB1. Any mimetics, derivatives, or homologs of SN50 may be used in the compositions, methods, and kits disclosed herein. The sequence of SN50 is AAVALLPAVLLALLAPVQRKRQKLMP (SEQ ID NO: 1). Generation and use of SN50 is described in U.S. Pat. No. 7,553,929.

cSN50 is a cyclized peptide combining the hydrophobic domain of the K-FGF signal sequence with the NLS of the p50 subunit of NFκB 1 and inserting a cysteine on each side of the NLS to form an intrachain disulfide bond. The amino acid sequence of cSN50 is AAVALLPAVLLALLAP-CYVQRKRQKLMPC (SEQ ID NO: 2). Any mimetics, derivatives, or homologs of cSN50 may be used in the compositions, methods, and kits disclosed herein.

cSN50.1 is a cyclized peptide having the sequence of cSN50 with the exception that the tyrosine at position 18 of cSN50, adjacent to the first cysteine, has been removed. Methods of making and using cSN50 are described, for example, in U.S. Pat. Nos. 7,553,929 and 6,495,518. The amino acid sequence of cSN50.1 is AAVALLPAVLLAL-LAPCVQRKRQKLMPC (SEQ ID NO:3). The tyrosine at position 18 was removed from the sequence of cSN50 to increase solubility. cSN50 is soluble at levels of ranging from 2.0 mg/mL to 40 mg/mL depending on the method of synthesis and purification whereas cSN50.1 is soluble at levels of at least 100 mg/ml. Any mimetics, derivatives, or homologs of cSN50.1 may be used in the compositions, methods, and kits disclosed herein. cSN50.1 beta is a cyclized peptide having the sequence of cSN50.1 with the exception that the lysine at the position 21 has been replaced by aspartic acid and the arginine residue at the position of 22 has been replaced by glutamic acid. The amino acid sequence of cSN50.1 Beta is AAVALLPAVLLALLAPCVQRDEQKLMPC (SEQ ID NO:4).

Modulating nuclear transport offers a new strategy for combating diseases and disorders associated with inflammation and/or dyslipidemia including vascular inflammation associated with hyperlipidemia and atherosclerosis. It is disclosed herein that nuclear transport represents a target for therapeutic suppression of such diseases and disorders. As described in the Examples below, targeting importin beta to control hyperlipidemia, the major cause of hepatobiliary and cardiovascular system complications, characterizes NTMs as prototypical members of a new class of dual function lipid-lowering and anti-inflammatory agents on the basis of the evidence presented here. These results establish the validity of targeting importin beta-mediated nuclear transport of SREBPs to reduce hypercholesterolemia, hypertriglyceridemia fatty liver, and atherosclerosis in a murine model of LDL receptor deficiency, and of also targeting importin alpha-mediated nuclear transport of SRTFs (e.g., NFκB, AP-1, NFAT, STAT1) for treating fatty liver, its attendant inflammation (steatohepatitis) and vascular inflammation manifested by atherosclerosis. The salient findings in support of this approach include: (i) application and characterization of a bifunctional NTM capable of binding importin beta, the sole nuclear transport adaptor for SREBPs; (ii) reduced nuclear transport of SREBP transcription factors and their subsequent expression, thereby attenuating SREBPs-regulated synthetic pathways for cholesterol, triglyceride, and fatty acid production in ldlr$^{-/-}$ mice fed a Western diet; (iii) concomitant prevention of fatty liver development and reduction of inflammatory biomarkers of hepatocellular injury, a hallmark of steatohepatitis; (iv) reduction of hyperglycemia by NTM linked to inhibition of nuclear transport of ChREBP, a bHLH-Zip domain transcription factor that activates genes encoding enzymes that convert excess carbohydrates into triglycerides rather than glycogen; (v) less weight gain in NTM-treated animals though food intake remained unchanged; and (vi) NTM attenuation of initiation and progression of atherosclerosis that exemplifies vascular inflammation evoked by metabolic insults. Furthermore, in the experiments described herein, NTM attenuated not only fatty liver but also its attendant inflammation (steatohepatitis) by normalizing its inflammatory biomarkers (elevated levels of the liver transaminases ALT and AST in plasma) and phosphorylated NF-κB RelA in liver cell nuclei. This was accomplished most likely through NTM's second function, namely, modulation of importins alpha that shuttle proinflammatory SRTFs to the nucleus. This second function of NTM also appears to play a role in vascular inflammation (atherosclerosis) evoked by metabolic insults.

These multi-pronged actions of NTM mitigated profound changes in several metabolic and proinflammatory pathways caused by a diet high in cholesterol and fat in the background of LDL receptor deficiency. Therefore, by targeting importin beta with NTM to modulate nuclear transport of SREBPs and ChREBP, as well as importin alpha with NTM to modulate nuclear transport of SRTFs, a new strategy for comprehensive reduction of hyperlipidemia, fatty liver, hyperglycemia, and atherosclerosis has emerged. An intense, short-term treatment with NTM resulted in long-term (1 year) suppression of Type 1 diabetes in NOD mice, a relevant model for human autoimmune disease, which is known to lead to hyperlipidemia and accelerated atherosclerosis. Moreover, continuing administration of NTM to ldlr$^{-/-}$ mice for 8 weeks, as demonstrated in this study, did not cause any apparent signs of general susceptibility to environmental pathogens. Our studies document that NTM displays a dual function, inhibition of nuclear transport of SREBPs with subsequent attenuation of their target genes responsible for hyperlipidemia and reduced nuclear transport of proinflammatory SRTFs exemplified by NFκB, which controls the inflammatory response. These results indicate that NTM not only controls nuclear access of proinflammatory SRTFs but also suppresses SREBP-1a, SREBP1c and SREBP-2 transcription factors that are primary regulators of cholesterol and fatty acids synthesis in liver. Since the expression of the LDL receptor depends on SREBPs, results in ldlr$^{-/-}$ mice indicate that NTM action circumvents the requirement for LDL receptor expression in reducing hyperlipidemia and attenuating atherosclerosis. The results disclosed herein indicate that hyperlipidemia and atherosclerosis are suppressed in a mouse model of familial hypercholesterolemia without overt signs of general toxicity. This form of intracellular therapy for disordered lipid metabolism may also show a salutary effect in humans to prevent severe consequences of hyperlipidemia for heart, liver, and brain.

Biological and Chemical Methods

Methods involving conventional molecular biology techniques are described herein. Such techniques are generally known in the art and are described in detail in methodology treatises such as Sambrook et al. ed., (2001) Molecular Cloning: A Laboratory Manual, 3rd ed., vol. 1-3, Cold Spring Harbor Laboratory Press, Cold Spring Harbor, N.Y.; and Ausubel et al. ed., (1992) (with periodic updates) Current Protocols in Molecular Biology, ed., Greene Publishing and Wiley-Interscience, New York.

Compositions for Treating Diseases and Disorders Associated with Inflammation and/or Dyslipidemia in a Subject Compositions (e.g., pharmaceutical compositions) described herein for treating diseases associated with inflammation and/or dyslipidemia, including hyperlipidemia, obesity, hypercholesterolemia, atherosclerosis, steatohepatitis, fatty liver, hyperglycemia, and metabolic syndrome include a therapeutically effective amount of a composition including a pharmaceutically acceptable carrier and a NTM in an amount effective for modifying (e.g., decreasing) entry into the nucleus of at least one transcription factor that includes but is not limited to NFκB, AP-1, NFAT, STAT1, SREBP1a, SREBP1c, and SREBP2, and ChREBP that utilize importins alpha and beta for nuclear transport, and treating or preventing the disease. For example, entry of at least one SREBP into the nucleus is reduced. In this example, the NTM reduces nuclear translocation of the nuclear forms of SREBP1a, SREBP1c, and SREBP2. Any suitable NTM may be used. Examples of NTMs include but are not limited to SN50, cSN50, cSN50.1 beta and cSN50.1. In some embodiments, an additional therapeutic agent such as an inhibitor of cholesterol synthesis (e.g., a statin) or inhibitor of cholesterol uptake (e.g. ezetimibe) may be administered at the same time, sequentially, or during the treatment course of the NTM. In such embodiments, any suitable existing or yet to be developed inhibitors of cholesterol transport or inhibitors of enzymes other than HMG Co-A reductase that are involved in synthesis of cholesterol and its uptake or synthesis and/or transport of triglycerides may be administered with an NTM.

Methods of Treating or Preventing Fatty Liver or Atherosclerosis in a Mammalian Subject A typical method of treating or preventing fatty liver or atherosclerosis in a mammalian subject includes administering a composition including a NTM to the mammalian subject in an amount effective for reducing importin alpha-mediated nuclear translocation of at least one SRTF, reducing importin beta-mediated nuclear translocation of SREBPs and ChREBP, and reducing dyslipidemia and inflammation in the mammalian subject. In the method, NTM reduces importin alpha-mediated nuclear translocation of the at least one SRTF and ChREBP and reduces importin beta-mediated nuclear translocation of SREBPs and ChREBP by binding to importin alpha and to importin beta, respectively. In an embodiment in which the subject has fatty liver or is predisposed to fatty liver, the at least one SRTF may be NFκB, and the inflammation may be steatohepatitis. Administration of the composition results in improved liver function, and may also result in reduced accumulation of cholesterol and triglycerides, a reduction in body weight and normalization of elevated blood glucose levels. In an embodiment in which the subject has atherosclerosis, administration of the composition results in a reduction of at least one atherosclerotic lesion in the subject, and the at least one SRTF can be one or more of: NFκB, AP-1, NFAT and STAT1. Administration of the composition prevents or reduces vascular inflammation associated with atherosclerosis. Any suitable NTM can be used, e.g., cSN50 having the sequence set forth in SEQ ID NO:2, or cSN50.1 having the sequence set forth in SEQ ID NO:3. To correct dyslipidemia without signs of significant inflammation of the liver (steatohepatitis) or vascular inflammation (atherosclerosis), cSN50.1 Beta having the sequence set forth in SEQ ID NO:4 can be used. The composition may be administered via any suitable route, e.g., orally. The therapeutic methods of the invention in general include administration of a therapeutically effective amount of a composition described herein to a subject (e.g., animal) in need thereof, including a mammal, particularly a human.

Methods of Treating or Preventing a Cardiovascular Disease, Metabolic Disease, or Liver Disease Associated with Inflammation and/or Dyslipidemia in a Subject A typical method of treating a cardiovascular disease, metabolic disease, or liver disease associated with inflammation and/or dyslipidemia in a mammalian subject includes administering to the mammalian subject a composition including NTM in an amount effective to reduce nuclear transport of at least one SREBP, reduce expression of the at least one SREBP, and reduce expression of at least one gene involved in cholesterol, triglyceride, or fatty acid synthesis. Such treatment will be suitably administered to subjects, particularly humans, at risk of, suffering from, or having, one or more diseases associated with inflammation and/or dyslipidemia, including, hypercholesterolemia, hypertriglyceridemia, atherosclerosis, hyperglycemia, metabolic syndrome, obesity, steatohepatitis or symptom thereof. The compositions herein may be also used in the treatment of any other disorders in which an excess of cholesterol or triglycerides or signaling, expression, activity, or nuclear entry of SRTFs and/or or SREBPs may be implicated.

In the methods, the at least one gene involved in cholesterol, triglyceride, or fatty acid synthesis or uptake can be, for example, HMG-CoA reductase (hmgcr), ATP citrate lyase (acly), fatty acid synthase-1 (fasn1), or Niemann-Pick C1-like1 protein (npc1l1) (or one or more thereof). Expression of the at least one gene can be reduced in the subject's liver. The NTM can be any suitable NTM, including, for example, cSN50 having the sequence set forth in SEQ ID NO:2, cSN50.1 having the sequence set forth in SEQ ID NO:3, or cSN50.1 Beta having the sequence set forth in SEQ ID NO:4. The composition can further include an additional therapeutic agent for treating or preventing the cardiovascular disease, metabolic disease, or liver disease, including, for example, an inhibitor of cholesterol synthesis (e.g., a statin) or an inhibitor of cholesterol uptake (e.g. ezetimibe). Typically, the composition is administered in an amount sufficient to decrease plasma cholesterol concentration and/or plasma triglyceride concentration. Additionally, administration of the composition may decrease one or more of: concentration of cholesterol in the liver, concentration of triglycerides in the liver, and concentration of fatty acids in the liver. If the subject is suffering from atherosclerosis and has one or more atherosclerotic lesions, administration of the composition may decrease the area of the one or more atherosclerotic lesions and decrease vascular inflammation.

In one embodiment, the invention provides a method of monitoring treatment progress. The method includes the step of determining a level of diagnostic marker such as plasma cholesterol and triglyceride, ALT, AST, (e.g., any target delineated herein modulated by a composition or agent described herein, a protein or indicator thereof, etc.) or diagnostic measurement (e.g., screen, assay) in a subject suffering from or susceptible to a disorder or symptoms thereof associated with, for example, obesity, hyperglycemia, hypercholesterolemia, hypertriglyceridemia, atherosclerosis, steatohepatitis, and metabolic syndrome in which the subject has been administered a therapeutic amount of a composition as described herein for treating the disease or symptoms thereof. The level of marker determined in the method can be compared to known levels of marker in either healthy normal controls or in other afflicted patients to establish the subject's disease status. In preferred embodiments, a second level of marker (e.g., ALT, AST, high sensitivity C-reactive Protein) in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

Also described herein are diagnostic and theranostic methods useful to determine whether the subject is susceptible to the treatment methods of the invention. The term "theranostics" generally refers to therapy-specific diagnostics, which is the use of diagnostic testing to diagnose the disease, choose the correct treatment regime for that disease, and monitor the patient response to therapy. Theranostic tests can be used to predict and assess drug response in individual patients, and are designed to improve drug efficacy by selecting patients for treatments that are particularly likely to benefit from the treatments. Theranostic tests are also designed to improve drug safety by identifying patients that may suffer adverse side effects from the treatment.

Kits

Described herein are kits for treating diseases or disorders associated with inflammation and/or dyslipidemia, including hyperlipidemia, cardiovascular diseases, atherosclerosis, hyperglycemia, hypercholesterolemia, fatty liver, steatohepatitis, and metabolic syndrome in a subject. A typical kit includes: a composition including a pharmaceutically acceptable carrier and a NTM in an amount effective for decreasing at least one of: cholesterol and triglyceride levels in the blood and liver, body weight, elevated blood glucose levels, atherosclerotic lesion size, as well as packaging, and instructions for use. In some embodiments, an additional compound such as an inhibitor of cholesterol synthesis or uptake may be included in the kit. The inhibitor of cholesterol synthesis may be, for example, a statin. The inhibitor of cholesterol uptake can be, for example, ezetimibe. Optionally, kits may also contain one or more of the following: containers which include positive controls, containers which include negative controls, photographs or images of representative examples of positive results and photographs or images of representative examples of negative results.

Administration of Pharmaceutical Compositions

The administration of a composition including a NTM in an amount effective for decreasing the levels of cholesterol and triglycerides in the blood and liver, decreasing atherosclerotic lesion size, decreasing body weight, decreasing elevated blood glucose levels, decreasing liver fat content, or increasing liver function for the treatment of, for example, atherosclerosis or hyperlipidemia, may be by any suitable means that results in a concentration of the therapeutic that is effective in decreasing the levels of cholesterol and triglycerides in the blood and liver, decreasing atherosclerotic lesion size, decreasing body weight, decreasing elevated blood glucose levels, decreasing liver fat content, or increasing liver function. In some embodiments, an additional compound such as an inhibitor of cholesterol synthesis or uptake may be administered. The inhibitor of cholesterol synthesis may be, for example, a statin or other modulator of cholesterol synthesis or triglyceride synthesis or transport as described above. The cholesterol uptake inhibitor can be, for example, ezetimibe or other modulator of this process. The NTM may be contained in any appropriate amount in any suitable carrier substance, and is generally present in an amount of 1-95% by weight of the total weight of the composition. The composition may be provided in a dosage form that is suitable for local or systemic administration (e.g., parenteral, subcutaneously, intravenously, intramuscularly, or intraperitoneally). The pharmaceutical compositions may be formulated according to conventional pharmaceutical practice (see, e.g., (Gennaro, A. R. ed. (2000) Remington: The Science and Practice of Pharmacy (20th ed.), Lippincott Williams & Wilkins, Baltimore, Md.; Swarbrick, J. and Boylan, J. C. eds. (1988-1999) Encyclopedia of Pharmaceutical Technology, Marcel Dekker, New York).

Compositions as described herein may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. In one embodiment, a composition as described herein is administered via osmotic pump. The composition may be administered orally in sublingual form or with a coating protecting the composition from gastrointestinal peptidases. The formulation and preparation of such compositions are well known to those skilled in the art of pharmaceutical formulation. Formulations can be found in Gennaro supra.

Compositions for parenteral use may be provided in unit dosage forms (e.g., in single-dose ampoules), or in vials containing several doses and in which a suitable preservative may be added. The composition may be in the form of a solution, a suspension, an emulsion, an infusion device, or a delivery device for implantation, or it may be presented as a dry powder to be reconstituted with water or another suitable vehicle before use. Apart from the active agent that treats or prevents hyperlipidemia, atherosclerosis, steatohepatitis, or metabolic syndrome, for example, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions described herein may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine), and poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly (caprolactone), poly(lactic acid), poly(glycolic acid) or poly (ortho esters) or combinations thereof).

Formulations for oral use include tablets containing the active ingredient(s) (e.g., a NTM such as cSN50.1, cSN50, cSN50.1 beta) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active therapeutic substance). The coating may be applied on the solid dosage form in a similar manner as that described in Swarbrick J. and Boylan, J. C. supra. At least two compounds for treatment of hyperlipidemia, atherosclerosis, steatohepatitis, or metabolic syndrome (e.g., a Nuclear Transport Modifier and an inhibitor of cholesterol synthesis such as a statin) may be mixed together in the tablet, or may be partitioned. In one example, the first active therapeutic is contained on the inside of the tablet, and the second active therapeutic is on the outside, such that a substantial portion of the second active therapeutic is released prior to the release of the first active therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment. Compositions as described herein can also be formulated for inhalation and topical applications. Optionally, an atherosclerosis or hyperlipidemia therapeutic may be administered in combination with any other standard atherosclerosis or hyperlipidemia therapy; such methods are known to the skilled artisan and described in Gennaro, A. R. ed. (1990) Remington's Pharmaceutical Sciences, Mack Publishing Company, Easton, Pa. In one example, an effective amount of a Nuclear Transport Modifier is administered in combination with a statin. Combinations are expected to be advantageously synergistic. Therapeutic combinations that decrease the level of cholesterol and/or triglycerides, for example, are identified as useful in the compositions, methods, and kits described herein.

The therapeutic methods described herein in general include administration of a therapeutically effective amount of a composition described herein to a subject (e.g., animal) in need thereof, including a mammal, particularly a human. Such treatment will be suitably administered to subjects, particularly humans, suffering from, having, susceptible to, or at risk for one or more of: hypercholesterolemia, hypertriglyceridemia, fatty liver, steatohepatitis, hyperglycemia, atherosclerosis, obesity, and metabolic syndrome. Determination of those subjects "at risk" can be made by any objective or subjective determination by a diagnostic test or opinion of a subject or health care provider.

Effective Doses

The compositions (pharmaceutical compositions) described herein are preferably administered to an animal (e.g., mammalian (such as human, ovine, bovine, canine, porcine, equine, etc.), reptilian, piscine, avian, etc.) in an effective amount, that is, an amount capable of producing a desirable result in a treated animal (e.g., decreasing the level of cholesterol or triglycerides in the blood or liver). Such a therapeutically effective amount can be determined according to standard methods. Toxicity and therapeutic efficacy of the compositions utilized in methods of the invention can be determined by standard pharmaceutical procedures. As is well known in the medical and veterinary arts, dosage for any one subject depends on many factors, including the subject's size, body surface area, age, the particular composition to be administered, time and route of administration, general health, and other drugs being administered concurrently.

EXAMPLES

The present invention is further illustrated by the following specific examples. The examples are provided for illustration only and should not be construed as limiting the scope of the invention in any way.

Example 1

Targeting Nuclear Transport in Hypercholesterolemia

Hyperlipidemia, fatty liver, and atherosclerosis contribute to cardiovascular and hepatobiliary morbidity and mortality worldwide. Previous studies have shown that genetic ablation of the transcription factor sterol response element-binding protein (SREBP) 1 in LDL receptor-deficient (ldlr$^{-/-}$) mice fed a Western diet high in cholesterol and fats prevents hyperlipidemia and atherosclerosis though liver steatosis remains unabated (Karasawa, T., et al., (2011) *Arterioscler Thromb Vasc Biol* 31, 1788-1795). We developed a cell-penetrating NTM that binds importin beta, the nuclear transporter for SREBPs, to inhibit their nuclear translocation, thereby reducing SREBPs-dependent transactivation of multiple genes controlling cholesterol, triglyceride, and fatty acid synthesis including 3-hydroxy-3-methylglutaryl-coenzyme A (HMG-CoA) reductase, the rate controlling enzyme in cholesterol synthesis, and Niemann-Pick C1-like1 (NPC1L1) protein, a key enterohepatic cholesterol absorption receptor. This modulation of importin beta-mediated SREBPs nuclear transport and SREBPs-controlled gene expression led to a striking decline in cholesterol and triglyceride levels in blood and liver while improving liver function, reducing body weight gain, and attenuating atherosclerosis. Improvement in liver function is also linked to attenuation of inflammation through inhibition of nuclear transport of NF-kappa B in the liver by NTM's second function. This function is based on binding NTM to importins alpha that mediate nuclear transport of NF-kappa B and other SRTFs. Moreover, elevated blood glucose was also lowered in treated mice, likely due to NTM-inhibited nuclear translocation of ChREBP. We suggest that bifunctional NTM that targets importin alpha and beta offers a new approach to comprehensive amelioration of hyperlipidemia, fatty liver with steatohepatitis, and atherosclerosis and their potential complications.

Hyperlipidemia is an integral factor in cardiovascular and hepatobiliary morbidity and mortality worldwide, which poses a huge burden on the estimated 33 million Americans with hypercholesterolemia and taking an annual death toll of over 800,000 due to cardiovascular disease. Derangement of lipid homeostasis is linked to excessive signaling to the nucleus by SREBPs 1a, 1c, and 2. SREBPs are transcription factors with a basic helix-loop-helix leucine zipper (bHLH-Zip) domain. A ~60 kDa NH2-terminal segment termed nuclear SREBP (nSREBP), that contains the bHLH-Zip region is translocated to the nucleus by a unique association with importin beta rather than first being complexed with one of the importins/karyopherins alpha that utilize importin beta for docking to the nuclear pore. Importin beta-mediated nuclear translocation of SREBPs culminates in activation of a set of genes that encode proteins involved in synthesis of cholesterol and its cellular binding pathways and in fatty acid, triglyceride, and phospholipid synthetic pathways.

The cardinal role for SREBPs in maintaining and/or altering lipid homeostasis is compellingly documented in previously reported genetic experiments. Overexpression of nuclear forms of SREBP 1a, 1c, and 2 in transgenic mice led to striking phenotypes of massive fatty liver and a 28-fold increase in cholesterol synthesis. This dramatic disruption of the autoregulatory loop of cholesterol and fatty acid synthesis caused by nuclear overload of SREBPs was extended to the model of accelerated atherosclerosis in LDL receptor-deficient ($ldlr^{-/-}$) mice. In this model for human familial hypercholesterolemia, the absence of SREBP1 prevented Western diet-induced hyperlipidemia and ameliorated atherosclerosis (Karasawa, T., et al., (2011) Arterioscler Thromb Vasc Biol 31, 1788-1795). However, while selective knockout of the srebpf1 gene reduced plasma cholesterol and triglyceride levels, improving the atherogenic lipoprotein profile and reducing atherosclerosis, the content of cholesterol and triglycerides in the liver was not reduced. This outcome is not surprising since it is known that selective deficiency of one SREBP gene may cause a compensatory overexpression of another SREBP gene, i.e. srebpf2, in the liver. We postulated that reversible attenuation of all dysregulated SREBP gene might offer comprehensive control of abnormal lipid homeostasis.

We pursued this goal by targeting a common nuclear transport pathway for the three nuclear SREBP isoforms. As SREBPS are ferried to the nucleus by a single carrier, importin beta (Lee, S. J., et al., (2003) Science 302, 1571-1575), we selected this protein as the target for therapeutic inhibition of all three SREBP isoforms. We first conducted studies to determine whether importin beta can be modulated by a NTM. This NTM was initially designed by us as a cell-penetrating peptide to block the family of importins/karyopherins alpha (Lin, Y. Z., et al., (1995) J Biol Chem 270, 14255-14258; Torgerson, T. R., et al., (1998) J Immunol 161, 6084-6092). NTM attenuates importin alpha-mediated nuclear transport in response to proinflammatory agonists by inhibiting nuclear translocation of SRTFs bearing an NLS. Surprisingly, although SREBPs lack an NLS, we found that NTM can still inhibit their nuclear translocation through direct interaction with the nuclear transport shuttle, importin beta. When NTM binds to importin beta, the bHLH-Zip region of SREBPs cannot latch onto this nuclear shuttle, preventing SREBPs delivery to the nucleus and the subsequent transcription of over 30 genes that encode cholesterol and triglyceride synthesizing enzymes and binding proteins. Hence, the striking outcome of NTM treatment of $ldlr^{-/-}$ mice fed a Western diet high in fat and cholesterol is a precipitous reduction of hypercholesterolemia, hypertriglyceridemia, fatty liver, atherosclerosis, body weight gain, and hyperglycemia.

Experimental Procedures

Preparation and Administration of Nuclear Transport Modifier (NTM) Peptides and Peptide Modules.

Cell-penetrating peptide cSN50.1 (2986 Da) and other peptides listed in Table 1 were synthesized and prepared as previously described (Liu, D., et al., (2009) Mol Ther 17, 796-802). Biotinylated NTM peptides and their constituent modules were prepared in the same manner, with biotin added to the amino terminus at the last step of synthesis. When necessary, a 5-7 hydrophilic amino acid tag was added to peptide modules to facilitate solubility. For i.p. administration, 200 µl aliquots containing 0.4 or 0.7 mg of cSN50.1 in saline was injected at 8 h or 12 h intervals. Alternatively, 10 mg cSN50.1 in 100 µl sterile $H_2O$ was administered subcutaneously from ALZET Osmotic Pumps (1007D) placed aseptically in interscapular areas. A bolus of 0.7 mg cSN50.1 in 100 µl saline was administered i.p. at weekly pump changes to assure steady NTM bioavailability. Dosage schedules were developed based on previous experimental protocols and half-life studies. Control mice received sterile saline in the same volumes as NTM.

Importins Pull-Down Assay.

Ten nmols of biotinylated NTM peptides or their constituent modules depicted in Table 1 (SN50, cSN50.1, N50, cN50.1, SSHR-1, SSHR-2) were incubated overnight at 4° C. with 1.5 mg of whole cell extract from unstimulated human Jurkat T cells or serum-starved human HepG2 cells lysed in binding buffer (10 mM HEPES at pH 7.9, 150 mM NaCl, 10 mM KCl, 2.5 mM $MgCl_2$, 1 mM EGTA, 1 mM DTT, 0.1% NP-40, 1% protease inhibitor cocktail). Lysate was cleared by centrifugation (16,000×g for 30 min at 4° C.) and transferred to a fresh tube containing high capacity Neutravidin beads (Thermo Scientific). After 4 h, beads were separated from lysate/peptide mixture by centrifugation (30 s at 1,000×g) and washed 3 times with binding buffer and 2 times with PBS. Beads were boiled for 10 min in SDS loading buffer, and protein content was analyzed by immunoblotting with a panel of anti-importins alpha and beta antibodies and anti-GAPDH (Abcam) as a cellular protein control.

Nuclear Transport Modifier/Importin Beta Competition Binding Assay.

Non-biotinylated SN50 peptide (at 0, 10, 30, 100 or 300 µM concentrations) was incubated overnight with 1 mg of human Jurkat T cell whole-cell extract at 4° C. Simultaneously, biotinylated SN50 peptide (10 nmols) was immobilized on high capacity Neutravidin beads at 4° C. overnight, then washed 3 times with PBS and 1 time with binding buffer to remove unbound biotinylated SN50. Binding mixture was precleared by centrifugation (16,000×g for 30 min at 4° C.) and transferred to a fresh tube containing washed high capacity Neutravidin beads complexed with immobilized biotinylated SN50 peptide. Immunoblot analysis of importin beta bound to beads was performed as described in the importins pull-down assay.

Human Hepatoma (HepG2) Cell Culture and Sterol Depletion.

HepG2 cells were maintained in DMEM supplemented with 10% FBS, 10 mM HEPES, penicillin (100 U/ml), and streptomycin (100 µg/ml) at 37° C. in 5% $CO_2$ in humid air. Before lysates were prepared for importins pull-down assays, HepG2 cells were starved overnight in DMEM containing 1% FBS. For rapid sterol depletion, cell monolayers were rinsed with Hank's buffered saline (HBSS) then incubated in DMEM supplemented with 5% delipidized FBS (Tissue Culture Biologicals 1 mg/dl cholesterol), 10 mM HEPES, penicillin (100 U/ml), streptomycin (100 µg/ml) and 1% hydroxypropyl-β-cyclodextrin (HPCD, MP Biomedicals) for 15 min. Monolayers were then rinsed in the same medium without HPCD and incubated in the same medium without HPCD but containing 10 µM MG132 and with 0, 10, or 30 µM cSN50.1 for 2 h. For gradual sterol depletion, cell monolayers were rinsed with HBSS then incubated in DMEM supplemented with 5% delipidized FBS, 10 mM HEPES, penicillin (100 U/ml), and streptomycin (100 µg/ml) with 0, 10, or 30 µM cSN50.1 for 24 h. MG132 (10 µM) was added 2 h before harvest.

Preparation and Immunoblot Analysis of Liver and HepG2 Cell Extracts.

Whole-cell extracts were prepared from snap-frozen livers by homogenization of liver pieces (100 mg) in ice cold RIPA buffer supplemented with protease and phosphatase inhibitors and 1% NP-40. Homogenates were centrifuged at 10,000×g for 30 min at 4° C. and supernatants used for immunoblotting. Nuclear and cytosolic extracts were prepared from frozen livers or HepG2 cells with the addition of phosphatase inhibitors. Liver pieces were disrupted in a Dounce hand homogenizer on ice without NP-40 and cells pelleted at 4000×g for 1 min before extract preparation. Extracts were analyzed by quantitative immunoblotting using monoclonal anti-SREBP1 (2A4, Novus), anti-phosphorylated NFκB p65 RelA (93H1, Cell Signaling), and anti-beta actin (AC15, Abcam) or polyclonal anti-SREBP1, anti-SREBP2, anti-NFκB p65 RelA, anti-NPC1L1, anti-Lamin B, anti-HDAC3 (Santa Cruz), anti-SREBP2 (Thermo), anti-GAPDH (Abcam) and anti-Lamin A/C (Cell Signaling) antibodies on Licor's Odyssey Infrared Imaging System. The positions of pSREBP and nSREBP bands in immunoblots of liver lysates were verified by immunoblotting with antibodies preincubated with a 5× molar excess of antibody-specific blocking peptides.

Quantitative PCR.

To quantify the expression of mRNA involved in cholesterol homeostasis, total RNA was isolated from livers of saline- and peptide-treated mice, and cDNA synthesized using the iScript™ cDNA Synthesis Kit (Bio-Rad). Assay mix was made by combining cDNA, Taqman® Gene Expression Master Mix (Applied Biosystems) and Taqman® gene expression probes for indicated genes according to the manufacturer's instructions. The data was analyzed using SDS2.3 software, and the Ct values were calculated using the RQ Manager Software (Applied Biosystems). All transcript levels were normalized to 18 S mRNA and values are expressed as $2^{-\Delta\Delta Ct}$ with the average of the saline-treated control group serving as the comparator.

Mouse Studies of Hyperlipidemia, Fatty Liver, and Atherosclerosis.

Six week old B6.129S7-Ldlrtm1Her/J female mice were purchased from Jackson Laboratories. Mice were fed a Western diet containing 21% milk fat and 0.15% cholesterol and maintained according to the guidelines for use and care of laboratory animals approved by the Vanderbilt University Institutional Animal Care and Use Committee. Mice and food were weighed at the beginning and end of each experiment. Blood chemistries were determined in fasting mouse plasma using an automated chemistry analyzer in the Vanderbilt Clinical Research Center. Total cholesterol and triglycerides in liver and cholesterol in feces were analyzed by standard methods in the Lipid Core Laboratory. Complete blood cell counts were performed in the Clinical Hematology Laboratory and flow cytometry analysis of lymphocytes subsets was. Cryostat sections of livers were stained with Oil-red-O. Atherosclerotic lesions and macrophages were analyzed in the aortic root by staining with Oil-red-O and MOMA-2, respectively. Average lesion area was determined using Imaging System KS300 2.0.

Statistical Analyses.

Statistical comparisons between groups were performed by log rank analysis, Student's t-test or ANOVA as appropriate. A p value less than 0.05 was considered significant.

Results

NTM Binds to Importin Beta, the Nuclear Transport Shuttle for SREBPs, and Inhibits Their Nuclear Import.

The nuclear forms of SREBPs, nSREBPs, lack a classic NLS recognized by importin alpha. Instead, nSREBPs are transported to the nucleus via an importin beta-mediated mechanism. As a first step in exploring the potential action of NTM toward nuclear translocation of SREBP transcription factors, we determined whether their nuclear transport shuttle, importin beta, interacts with NTM. In contrast to importins alpha, which recognize NLS on nuclear cargo, importin beta recognizes SREBP2 by binding its highly conserved bHLH-Zip region dimer through mostly hydrophobic interactions. The NTMs used in this study are first-in-class 26 or 28 amino acid fragment-linked peptides derived from the signal sequence hydrophobic region (SSHR) of human Fibroblast Growth Factor 4 and from the NLS of human nuclear factor kappa B1. The SSHR enables facile intracellular delivery of these cell-penetrating peptides to modulate nuclear transport of SRTFs in circulating blood cells as well as organs. By occupying NLS-binding pockets on importins alpha, NTM prevents their interaction with SRTFs that encompass nuclear factor kappa B (NFκB), activator protein-1 (AP-1), nuclear factor of activated T cells (NFAT), and signal transducer and activator of transcription 1 (STAT1). The cyclized form of NTM, cSN50.1, is a cell-penetrating peptide that is easily delivered to the blood cells, liver, spleen, pancreas, and lungs due to its high solubility (100 mg/ml). NTM protects these organs from microbial and autoimmune inflammation, including Type 1 diabetes. In the nucleus, SRTFs activate a myriad of genes that encode mediators of inflammation; NTM suppresses this process in cultured cells and in vivo.

As presented in Table 1, we employed two isoforms of NTM, full length peptides SN50 and cSN50.1 that comprise a SSHR as a membrane-translocating motif and an NLS (27).

TABLE 1

Nuclear Transport Modifier (NTM) peptides[1]
(sequences of NTM peptides used to conduct the
study). Hydrophobic regions of the SSHR domain are distinguished from the cluster of basic amino acids (NLS). SSHR derived peptides showed limited solubility in aqueous solution and were equipped with solubility tag. For binding assays all peptides were labeled with biotin.

| | SSHR[2] | NLS[3] |
|---|---|---|
| SN50 | AAVALLPAVLLALLAP (SEQ ID NO: 5) | VQRKRQKLMP (SEQ ID NO: 6) |
| cSN50.1 | AAVALLPAVLLALLAP (SEQ ID NO: 5) | CVQRKRQKLMPC (SEQ ID NO: 7) |
| cSN50.1 Beta | AAVALLPAVLLALLAP (SEQ ID NO: 5) | CVQRDEQKLMPC (SEQ ID NO: 8) |
| N50 | | VQRKRQKLMP (SEQ ID NO: 6) |
| cN50.1 | | CVQRKRQKLMPC (SEQ ID NO: 7) |
| SSHR-1[4] | AAVALLP (SEQ ID NO: 9) | |
| SSHR-2[4] | | AVLLALLAP (SEQ ID NO: 10) |

[1]N-biotinylated versions of above peptides were used in binding and competition assays

[2]Signal Sequence Hydrophobic Region

[3]Nuclear Localization Sequence

[4]Solubility tag added to the N-terminus of the peptide

The SN50 peptide is a linear combination of SSHR and NLS whereas cSN50.1 has a cyclized NLS, formed by the addition of two cysteine residues resulting in an intrapeptide disulfide bond. cSN50.1 Beta has NLS module mutated to abolish importin alpha binding function. The N50 and cN50.1 peptides comprise the NLS segments of SN50 and cSN50.1, respectively. The peptides were biotinylated and incubated with cell lysates derived from human Jurkat T cells or human hepatoma HepG2 cells followed by the addition of streptavidin-coated beads to capture biotinylated NTM/importin complexes. We used human Jurkat T cells to analyze the interaction of NTM with importins alpha and beta because T lymphocytes are involved in hepatitis and vascular inflammation and our initial study of nuclear transport mediated by importin alpha was performed in these cells. The two full-length biotinylated NTMs (SN50 and cSN50.1) interacted with importins alpha 1, 4, and 5 but not with the control cytoplasmic marker protein GAPDH. Biotinylated cSN50.1 Beta did not react with importins alpha. Surprisingly, the full length peptides also interacted with importin beta. In contrast, biotinylated N50 and cN50.1 peptides that reproduce the basic NLS derived from NFκB1 (p50) but do not contain a SSHR sequence, did not react with importin beta but did maintain reactivity with importins alpha 1, 4, and 5. Since N50 and cN50.1 peptides lack a SSHR, we inferred that this motif provided a second binding function to NTM, namely interaction through its hydrophobic residues with importin beta. A similar binding pattern was recorded by us with cell lysates derived from human HeLa cells. We localized the importin beta-binding function to SSHR-2 that adjoins the NLS (Table 1). Binding to importin beta was specific and reversible since free, non-biotinylated SN50 peptide competitively inhibited biotinylated SN50 peptide binding to importin beta. Thus, fortuitously, NTM displayed a second recognition function by binding to importin beta through SSHR-2. This second function of NTM indicated that it could also modulate importin beta-mediated nuclear transport of SREBPs that carry a bHLH domain.

After characterizing this new binding function for NTM in respect to importin beta, the nuclear transporter for SREBPs, we tested the effect of NTM on translocation of SREBPs to the nucleus in human liver-derived hepatoma HepG2 cells. We found that NTM (SN50 and cSN50.1) interacted with importin beta in human hepatoma HepG2 cell extracts, but not with the control protein GAPDH. We then analyzed nuclear transport of SREBP1 and SREBP2 in sterol-depleted HepG2 cells. In response to a decreased intracellular level of sterols, their sensor Scap initiates translocation of ER membrane-bound SREBPs to the Golgi apparatus where two proteases split off the mature, nuclear forms that are recognized in the cytoplasm by importin beta and transported to the nucleus. Treatment with cSN50.1 for 2 h prevented this last step, thereby reducing nuclear accumulation of nSREBP1 and nSREBP2. At the same 2 h time point, precursor forms of SREBP1 and SREBP2 (pSREBP1 and pSREBP2) remained unchanged in NTM-treated cells as compared to control. Moreover, processing of precursor forms of SREBPs to their nuclear (mature) forms was also unaffected by NTM as documented by their presence in the cytosolic fraction. The effect of NTM on nuclear translocation of SREBP1 was demonstrated in two different intracellular sterol-depleting conditions. After using HPCD to rapidly deplete cells of sterols, the effect of cSN50.1 was concentration-dependent, but when sterols were gradually depleted by prolonged incubation in medium containing delipidized FBS, maximum reduction of the nuclear pool of nSREBP1 was achieved with co-incubation of only 10 μM cSN50.1 and a higher concentration (30 μM) of this NT did not further reduce nSREBP1 in the nucleus by a significant amount. Notably, NTM did not completely reduce nuclear transport of SREBPS in either protocol. Thus, under the experimental conditions of our studies, inhibition of importin beta-mediated nuclear transport of SREBPs is incomplete, allowing their partial transport. Nevertheless, these studies support the newly discovered second function of NTM, namely, time- and concentration-dependent attenuation of importin beta-mediated nuclear transport of nSREBPs. We next asked the question: does NTM treatment reduce SREBPs expression and action in the liver?

In Vivo Reduction of SREBPs and their Target Genes that Encode Cholesterol-, Triglyceride-, and Fatty Acid-Synthesizing Enzymes and Cholesterol Uptake Proteins.

We targeted nuclear transport with NTM in vivo in atherosclerosis-prone $ldlr^{-/-}$ mice fed a Western diet (21% milk fat and 0.15% cholesterol) by treating them with cSN50.1 peptide (see Table 1). Initially, to test the effect of NTM on hypercholesterolemia, there were two control groups, animals treated with either a non-cell penetrating peptide comprised of only the NLS (cN50.1) diluted in saline as a vehicle or saline alone. The results of the experimental endpoints analyzed below did not differ significantly in these two control groups. Therefore, subsequent experiments were conducted with control animals receiving saline only. As the liver is the main organ in which SREBP transcription factors act as the master regulators of lipid homeostasis, we examined their expression in liver extracts derived from Western diet-fed $ldlr^{-/-}$ mice treated for 4 and 8 weeks with NTM or saline (control). Both precursor and nuclear forms of SREBP1 and SREBP2 proteins were reduced in NTM-treated $ldlr^{-/-}$ mice as compared to saline-treated controls ($p<0.05$ and $p<0.005$, respectively) (FIGS. 1A and B). This reduction in SREBPs protein expression was paralleled by progressively reduced transcripts for both SREBP1 (srebf1) and SREBP2 (srebf2) ($p<0.05$ after 4 weeks; $p<0.005$ and $p<0.0005$, respectively after 8 weeks) in the livers of NTM-treated mice (FIG. 1C). As SREBPs regulate their own cognate genes through an autoregulatory feed forward loop, in addition to more than 30 other known genes that encode the cascade of cholesterol and fatty acid synthesis enzymes and cholesterol uptake proteins, we also analyzed transcripts for some of these genes. We noted progressive reduction of mRNA for HMG-CoA reductase (hmgcr), the rate-controlling enzyme in cholesterol synthesis and a target of statins (FIG. 1C), reaching a significantly decreased level of expression after 4 weeks ($p<0.05$) and 8 week of treatment ($p<0.0005$). Likewise, representative transcripts encoding other SREBP-controlled genes, ATP citrate lyase (acly) and fatty acid synthase-1 (fasn1) were significantly reduced ($p<0.05$ and $p<0.005$, respectively), after 8 weeks of NTM treatment. The latter gene is regulated by SREBP1c, a dominant isoform in human and mouse livers. However, genes encoding proteins responsible for cholesterol enterohepatic efflux, ABCG5 (abcg5) and ABCG8 (abcg8), were not reduced (FIG. 1C). Thus, NTM attenuated not only expression of SREBP transcription factors but also their target genes involved in cholesterol, triglyceride, and fatty acid synthesis (Horton, J. D., et al., (2003) Proceedings of the National Academy of Sciences of the United States of America 100, 12027-12032). In addition, we noted significant NTM-induced reduction of SREBPs-regulated NPC1L1 protein, a key enterohepatic cholesterol absorption receptor and a portal for hepatitis C virus entry to liver cells ($p<0.005$).

NTM reduction of SREBPs in the liver is accompanied by a decline in cholesterol and triglycerides in plasma and liver and prevention of fatty liver and weight gain in ldlr$^{-/-}$ mice fed a western diet. Consistent with a significant reduction of srebpf1 and srebpf2 gene expression after only four weeks of treatment with NTM (see FIG. 1C), plasma cholesterol and triglyceride levels were significantly reduced in ldlr$^{-/-}$ mice fed Western diet as compared to the control groups (FIG. 2A). Results from mice treated with control peptide cN50 were not different from those of mice given saline as a control. Also, NTM-treated animals gained less weight than those in the control group, though the food intake of Western diet-fed ldlr$^{-/-}$ mice was the same in both groups (FIG. 2H). Strikingly, the mean cholesterol level was significantly lower (by 40%) in mice treated with NTM ($p<0.005$) as compared to the control group, where it reached almost 1,500 mg/dL after eight weeks of Western diet (FIG. 2A). Moreover, plasma triglycerides remained at a steady level in NTM-treated mice while control mice had doubled their triglyceride levels. The NTM-induced reduction of plasma cholesterol in NTM-treated mice was associated with a decrease in proatherogenic LDL and VLDL cholesterol fractions (FIG. 2B). These results indicate that the dynamics of elevated blood cholesterol and triglyceride reduction by NTM after 4- and 8-week treatment correlates with the time-dependent attenuation of SREBP gene expression documented in FIG. 1C.

In parallel to the precipitous decline in plasma cholesterol and triglyceride levels, NTM reduced the abnormal accumulation of cholesterol and triglycerides in the liver by 45% and 40%, respectively (FIG. 2C), while increasing intestinal disposal of cholesterol by 35% (FIG. 2D), consistent with reduction of NPC1L1 protein in NTM-treated mice. Consequently, the overall fat content in the liver was dramatically reduced (FIG. 2E) though mice in both groups consumed the same amount of high fat and high cholesterol-containing food (FIG. 2H). Thus, treatment with NTM corrected disordered lipid metabolism due to excessive dietary intake of cholesterol and fats in the background of LDL receptor deficiency.

Figure 5:
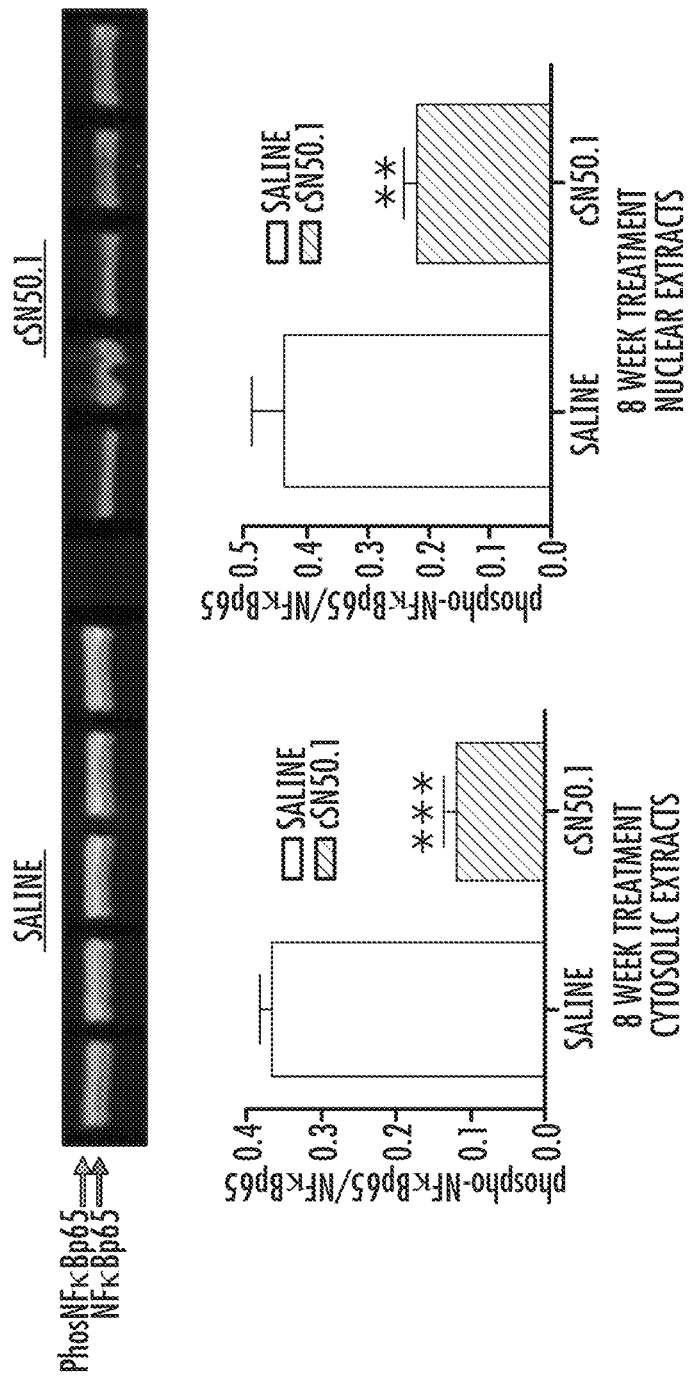
FIG. 5 is an immunoblot and a pair of graphs showing suppression of NFκB RelA phosphorylation in liver extracts from ldlr$^{-/-}$ mice fed a Western diet and treated with saline or cSN50.1 peptide for 8 weeks. Immunoblot of cytosolic extracts from control (saline) and cSN50.1-treated mice. Quantitative analysis of immunoblot indicates significant suppression of phosphorylated NFκB RelA (green) expressed as its relative ratio to total RelA (red) in both cytosolic and nuclear extracts. ( denotes p<0.005 and * denotes p<0.0005 by Student's t test).

NTM also reduced elevated liver alanine and aspartate transaminases (ALT and AST) in Western diet-fed ldlr$^{-/-}$ mice (FIG. 2F), possibly by attenuating the liver inflammatory response to growing fat content. Similar to saline-treated controls, animals receiving control cN50 peptide displayed elevated levels of liver transaminases. These biomarker changes are indicators of attenuated steatohepatitis and are also significantly reduced by NTM in other models of liver inflammation. Therefore, we analyzed the fatty livers of Western diet-fed ldlr$^{-/-}$ mice for activation and nuclear transport of NFκB RelA. This master regulator of inflammatory genes is kept in check by IκBα and by ubiquitin modifier A20 protein. These control mechanisms are altered in Western diet-fed ldlr$^{-/-}$ mice treated with saline as they displayed the active, phosphorylated form of NFκB RelA in cytosolic and nuclear fractions of liver cells while it was reduced in the livers of NTM-treated mice (FIG. 5). These experiments indicate a dual function of NTM: (i) inhibition of nuclear transport of SREBPs with subsequent reduction of their target genes responsible for hyperlipidemia (FIG. 1), and (ii) inhibition of nuclear transport of proinflammatory SRTFs exemplified by NFκB, which controls the inflammatory response (FIG. 5).

Reduction of Hyperglycemia in NTM-Treated Ldlr$^{-/-}$ Mice Fed a Western Diet.

Remarkably, an 8-week treatment with NTM also normalized elevated blood glucose levels in Western diet-fed ldlr$^{-/-}$ mice (FIG. 2G). Carbohydrate response element binding protein (ChREBP) is a glucose-activated transcription factor involved in the development of metabolic syndrome (Iizuka, K., and Horikawa, Y. (2008) Endocrine journal 55, 617-624). ChREBP belongs to the same bHLH-Zip family as SREBPs and regulates expression of genes involved in glycolysis, lipogenesis, and gluconeogenesis that convert excess carbohydrates into triglycerides rather than glycogen. Therefore, we examined whether NTM could reduce glucose-induced nuclear transport of ChREBP and found that NTM (cSN50.1 at 30 µM) attenuated nuclear translocation of ChREBP in human liver-derived hepatoma HepG2 cells. In ldlr$^{-/-}$ mice fed a Western diet, hyperglycemia is associated with elevated levels of triglycerides thereby forming "the deadly combination" (Brown, M. S., and Goldstein, J. L. (2008) Cell metabolism 7, 95-96). Restoration of glucose and triglycerides to physiologic levels by NTM, which attenuates nuclear translocation of SREBPs and ChREBP, extends the action of NTM to the major facets of metabolic syndrome. Cumulatively, these data indicate that hypercholesterolemia, hypertriglyceridemia, hyperglycemia, fatty liver, and weight gain are reduced in NTM-treated ldlr$^{-/-}$ mice fed a Western diet.

Figure 3A:
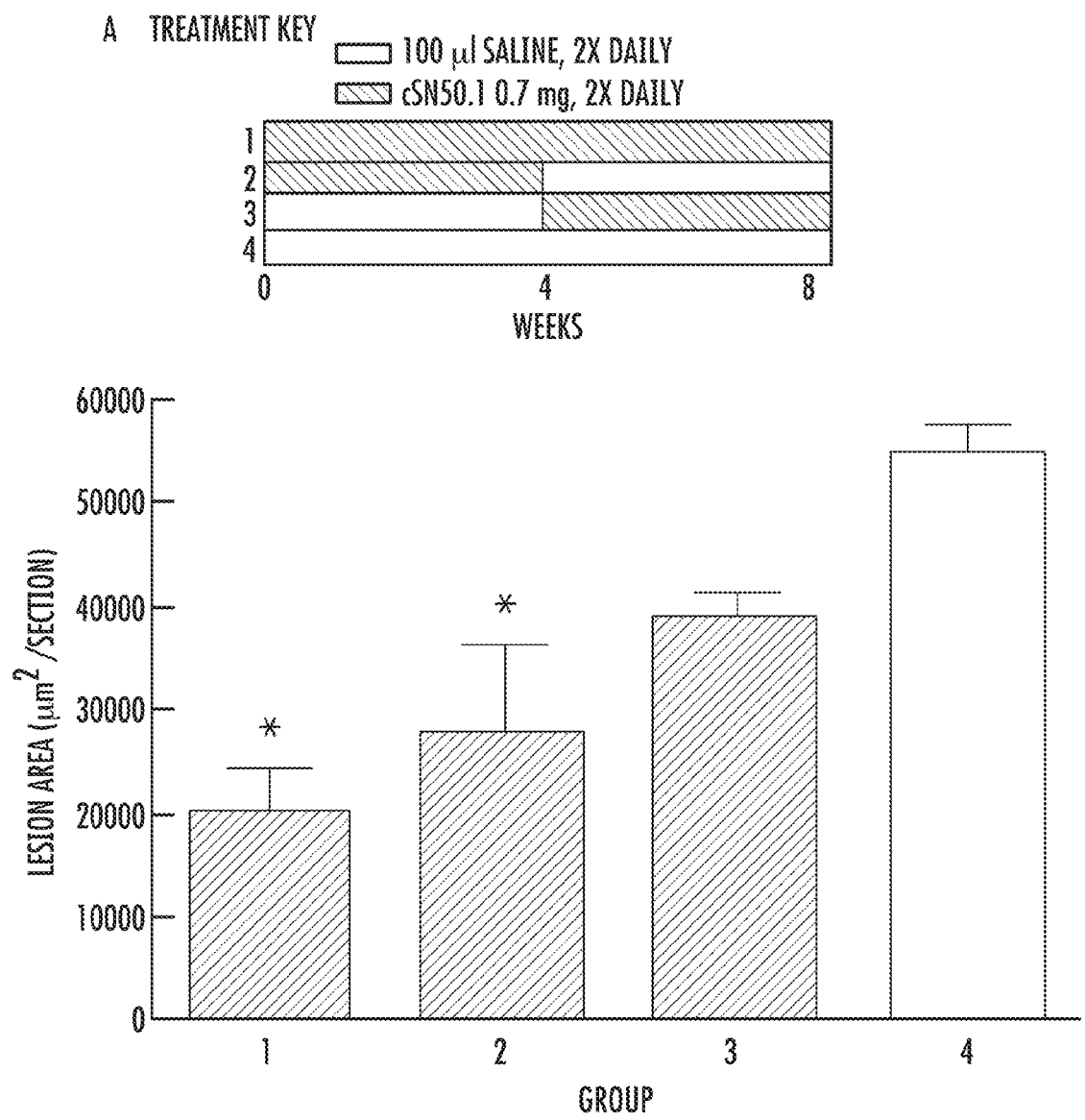
FIGS. 3A-3C are a pair of graphs and a pair of micrographs of the aortic sinus showing that atherosclerosis is reduced in Western diet-fed ldlr$^{-/-}$ mice treated with NTM.
Figure 3B:
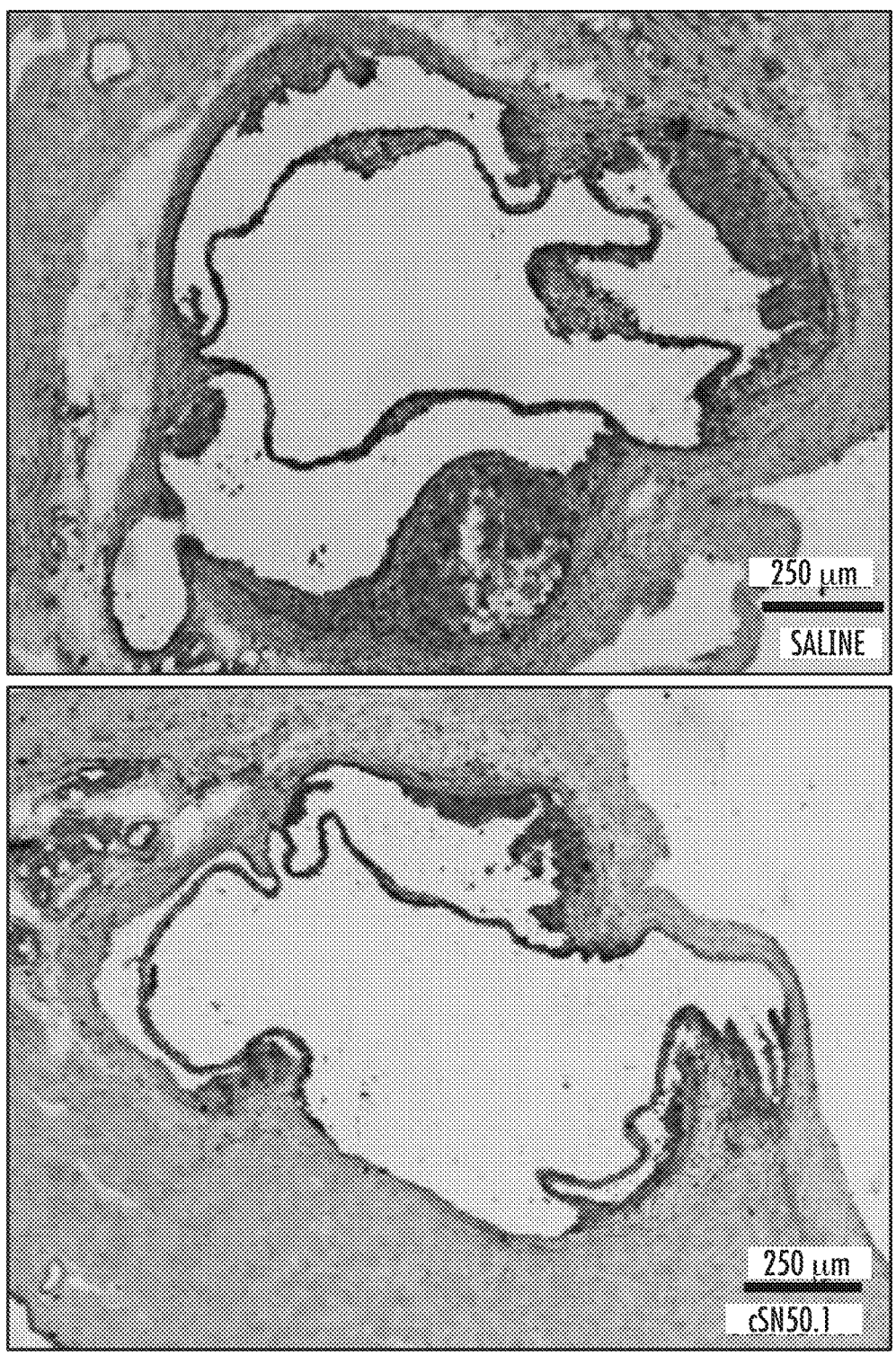
Figure 3C:
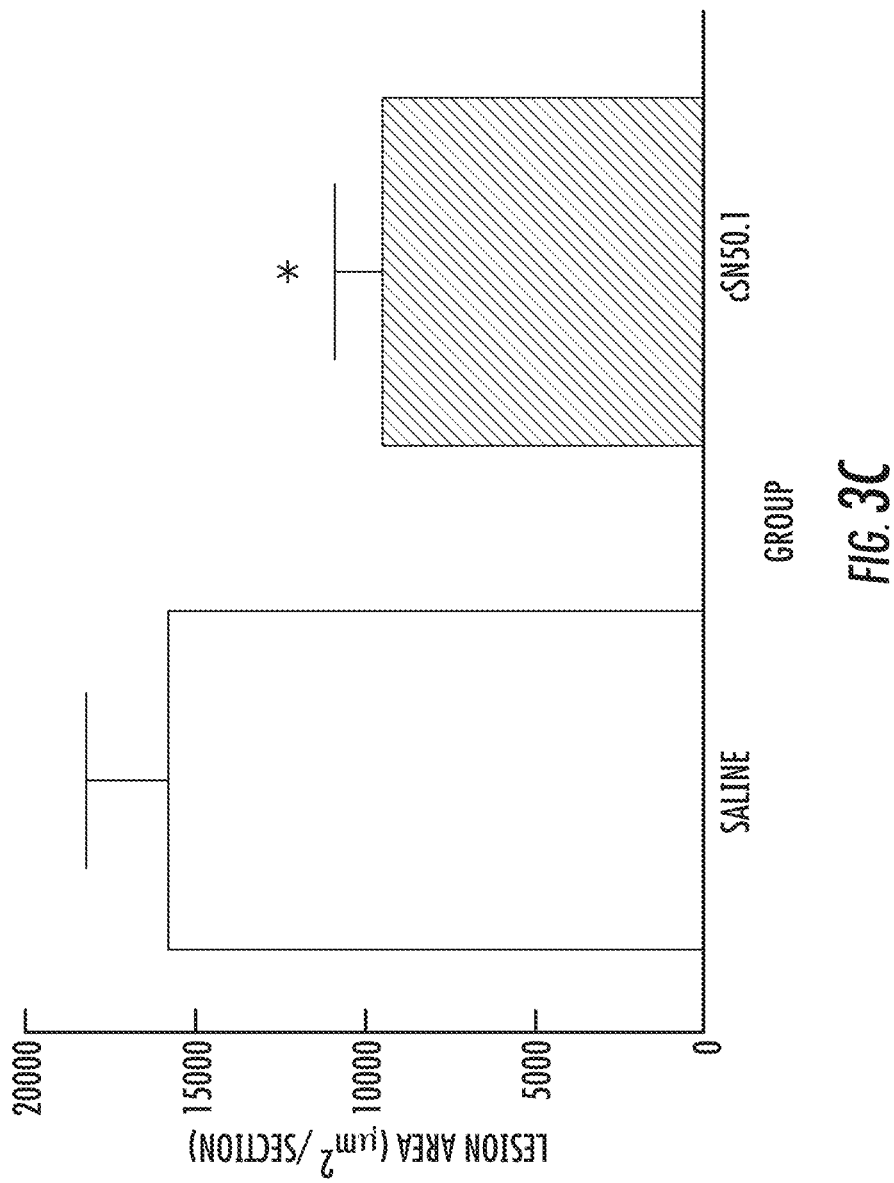
Figure 4A:
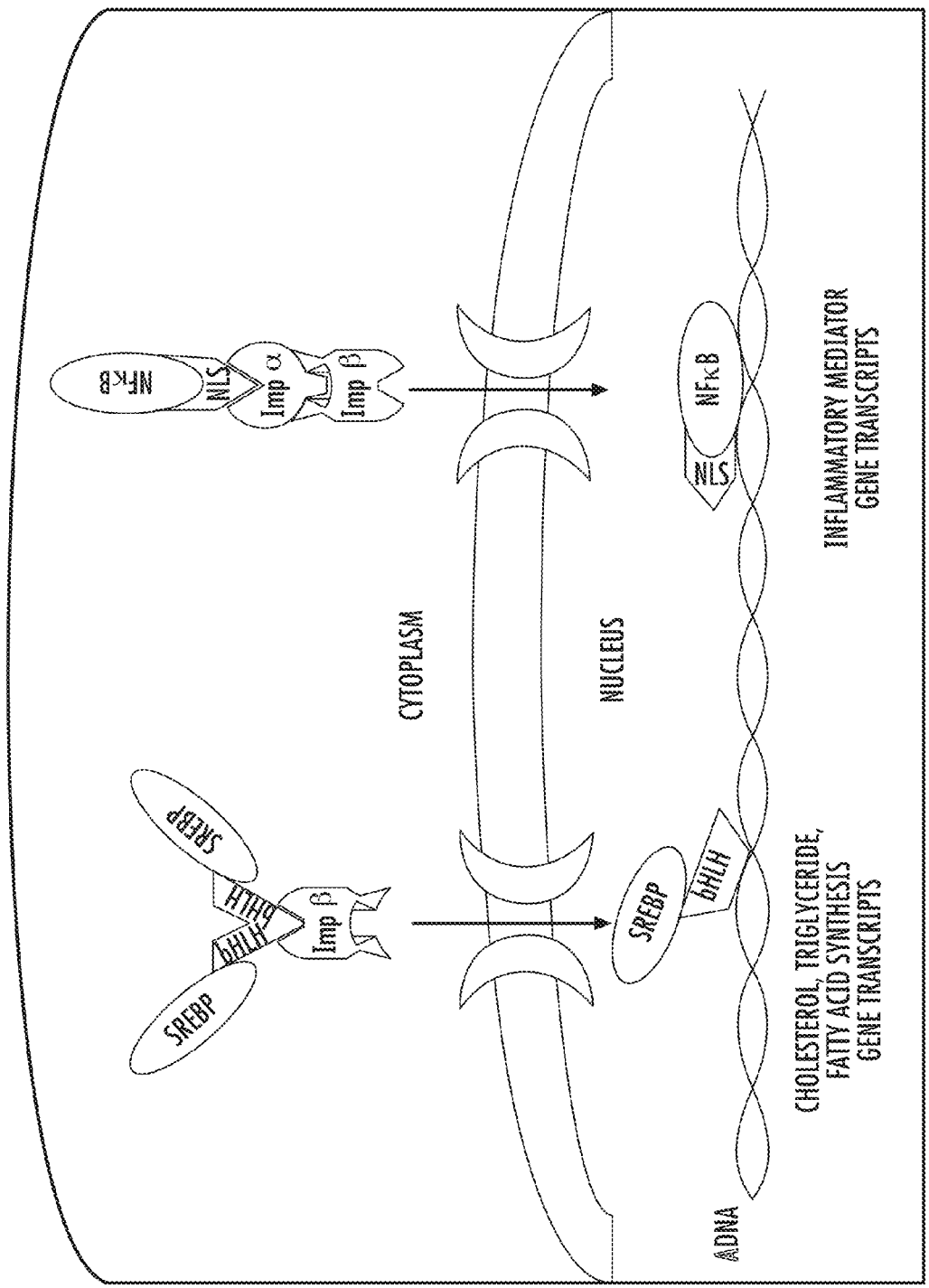
FIGS. 4A-4B are schematic illustrations of two pathways of nuclear import and their inhibition by a bifunctional nuclear transport modifier (NTM).
Figure 4B:
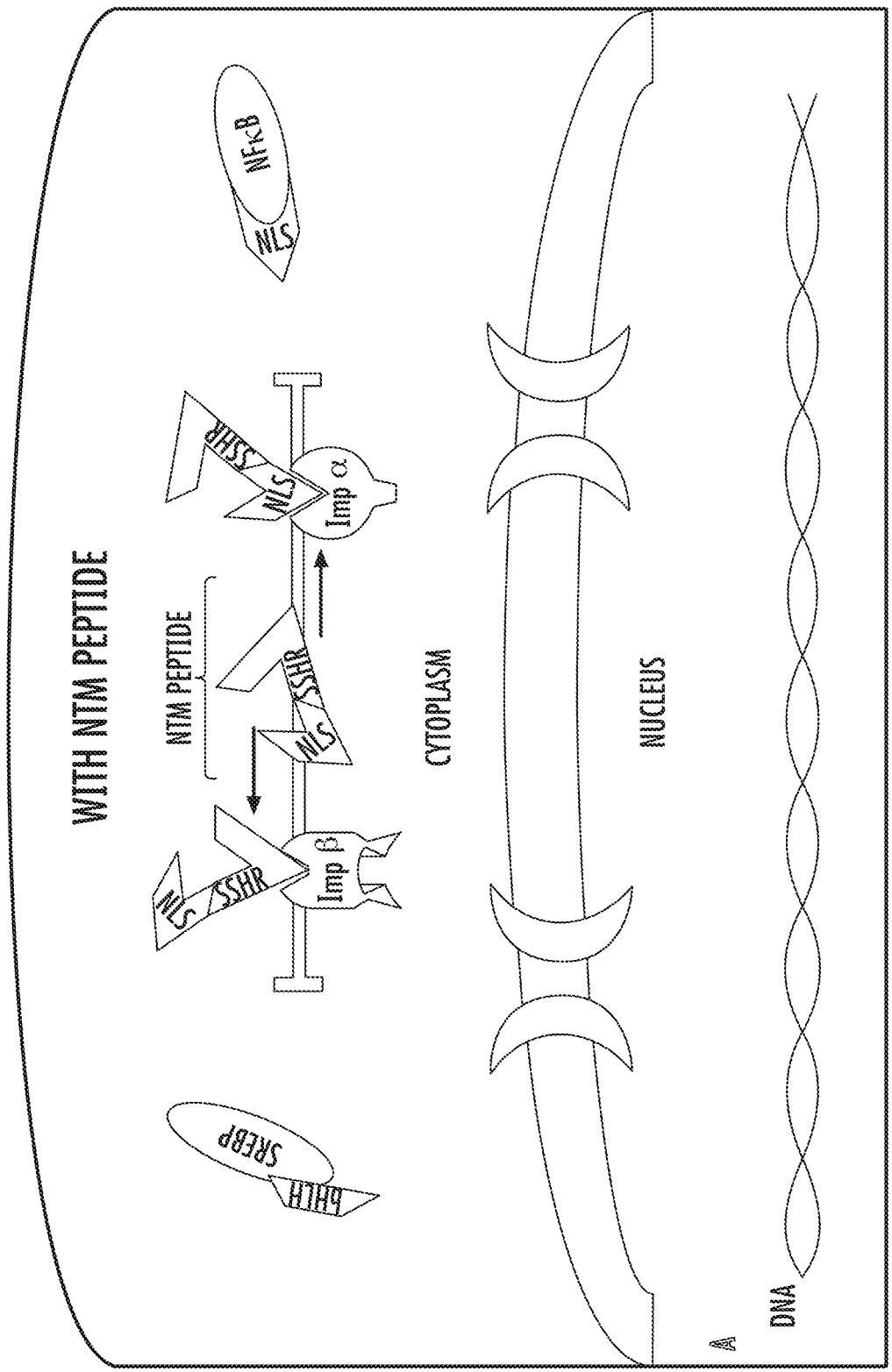
Figure 6:
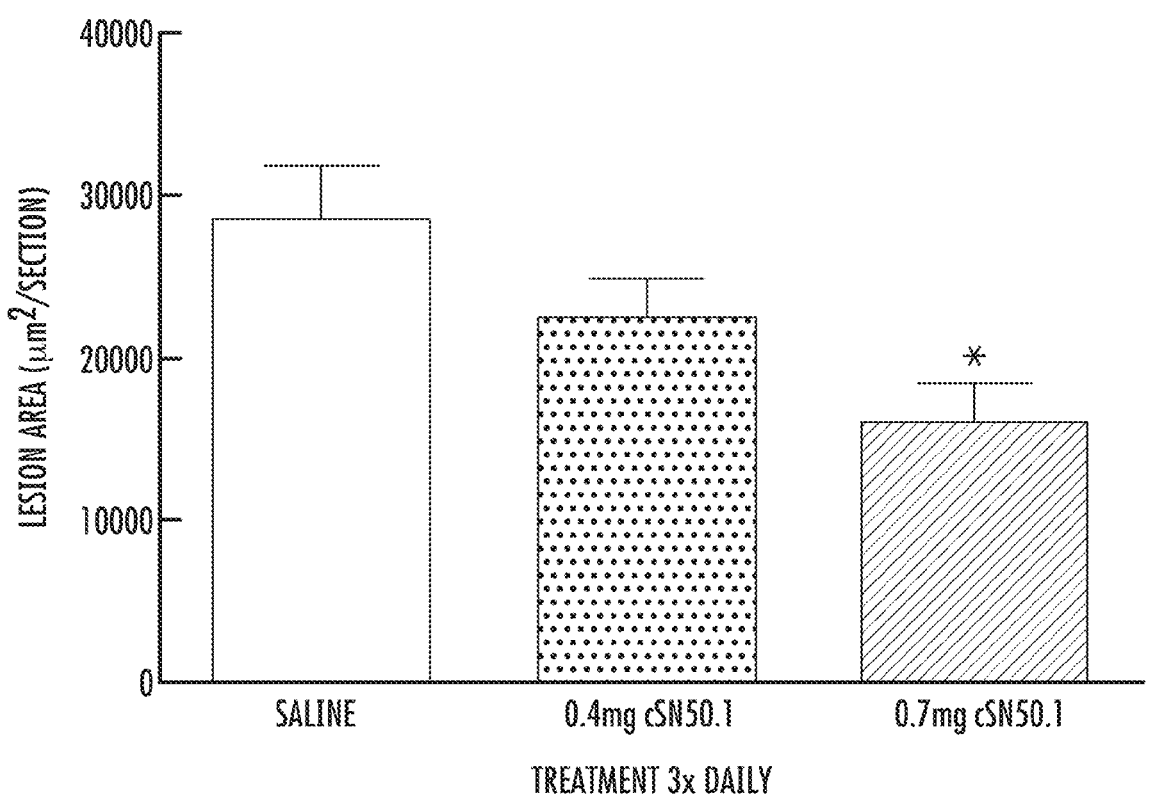
FIG. 6 is a graph showing that a reduction of atherosclerosis in Western diet-fed ldlr$^{-/-}$ mice treated with NTM is dose dependent. Average lesion area determined by Oil-Red-O analysis of the aortic sinus. Mice receiving 0.7 mg/mouse of cSN50 peptide three times daily by i.p. injection for 4 weeks had a significant reduction in atherosclerotic lesion size compared to the saline-treated group. Mice that received 0.4 mg/mouse three times daily were not protected from atherosclerosis. Average lesion area determined by Oil-Red-O analysis of the aortic sinus (* denotes p<0.05 by Kruskal Wallis with a Dunnett's Multiple Comparison post-test).

Attenuation of Atherosclerosis. Overexpression of SREBP1a and SREBP1c in the livers of ldlr$^{-/-}$ mice leads to accelerated atherosclerosis whereas SREBP 1a deficiency abrogates this process. Therefore, suppressing importin beta-mediated nuclear transport and the subsequent reduction in SREBPs expression may offer a new strategy not only for reducing hypercholesterolemia, hypertriglyceridemia, hyperglycemia, and fatty liver but also for preventing vascular inflammation associated with atherosclerosis. Hence, we studied the impact of NTM treatment on development of atherosclerosis in Western diet-fed ldlr$^{-/-}$ mice. These mice develop atherosclerosis mimicking that in human familial hypercholesterolemia in which genetic defects in LDL receptor function increase the risk of early heart attack more than 10-fold. Initiation and progression of atherosclerosis was assessed in the aortic root of mice by Oil-Red-O imaging. Consistent with the striking suppression of plasma cholesterol and triglyceride levels (see FIG. 2A), ldlr$^{-/-}$ mice displayed a 63% reduction in atherosclerotic lesions following an 8-week treatment regimen of twice daily i.p. injections of cSN50.1 peptide (0.7 mg/mouse, Group 1 in FIG. 3A), compared to saline-treated controls (Group 4, p<0.05). Another control group treated with cN50 peptide lacking the importin beta binding site had similar lesions to saline-treated control mice. NTM-induced reduction of atherosclerotic lesions was documented by histological examination of aortic roots (FIG. 3B). The atherosclerosis suppressing effect of NTM was concentration- and time-dependent, as mice receiving a lower dose of cSN50.1 (0.4 mg) were not protected (FIG. 6). Remarkably, NTM treatment in either the first four weeks or the last four weeks of the Western diet protocol reduced atherosclerotic lesions by approximately 50% (p<0.05) or approximately 30%, respectively (FIG. 3A). The latter result indicates the potential for NTM to arrest or reverse preformed atherosclerotic lesions. An alternative route of NTM administration via subcutaneous delivery from osmotic pumps changed weekly for 4 weeks as described in the Experimental Procedures, also significantly suppressed development of early lesions (FIG. 5C). Cumulatively, NTM treatment of hypercholesterolemic ldlr$_{-/-}$ mice is strikingly effective in a dose- and time-dependent manner, irrespective of delivery route, to prevent the initiation and reduce the progression of atherosclerosis.

While this process depends on migration of macrophages and formation of cholesterol-laden foam cells, selective ablation of SREBP1a in these cells is insufficient to stem atherosclerosis development in ldlr$^{-/-}$ mice fed a Western diet. Since NTM is readily delivered to blood cells and multiple organs, we examined the effect of NTM on macrophage distribution in and around the atherosclerotic lesions. MOMA-2 staining demonstrated that lesions were composed mainly of macrophages indicating that 4-week treatment with NTM does not change the main cellular components of the lesion. However, in NTM-treated mice, many of the macrophages failed to populate the atherosclerotic lesion as in saline-treated control animals. This early effect on macrophage trafficking around the growing atheroma is consistent with decreased macrophage migration into the peritoneal cavity observed in NTM-treated ldlr$^{-/-}$ mice given i.p. injections of thioglycolate. These observations are consistent with our previous findings that NTM significantly attenuates chemokine expression. NTM treatment reduced several chemokines (monocyte chemokine protein-1, macrophage inflammatory protein-2 keratinocyte-derived chemokine, interferon-induced protein-10, and fractalkine) in acute lung, liver and kidney inflammation models. Moreover, a SREBPs-regulated change in the ratio of membrane cholesterol and phospholipids may be involved in NTM-induced inhibition of macrophage migration. Despite this caveat, analysis of blood cell populations and blood chemistries did not reveal any significant changes other than those shown in mice given NTM as compared to control animals after 8 weeks of treatment, and there were no overt signs of infection or illness in treated animals.

Other Embodiments

Any improvement may be made in part or all of the compositions, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A composition comprising a pharmaceutically acceptable carrier and an isolated peptide or polypeptide comprising an amino acid sequence selected from the group consisting of: the amino acid sequence set forth in SEQ ID NO:3, and the amino acid sequence set forth in SEQ ID NO:4.

2. The composition of claim 1, further comprising an additional therapeutic agent.

3. The composition of claim 2, wherein the additional therapeutic agent is an inhibitor of cholesterol synthesis.

4. The composition of claim 3, wherein the inhibitor of cholesterol synthesis is a statin.

5. The composition of claim 2, wherein the additional therapeutic agent is an inhibitor of cholesterol uptake.

6. The composition of claim 5, wherein the inhibitor of cholesterol uptake is ezetimibe.

7. The composition of claim 1, wherein the isolated peptide or polypeptide binds importin beta.

8. A method of treating at least one of hyperlipidemia, fatty liver, steatohepatitis, obesity, hyperglycemia, metabolic syndrome, cardiovascular disease, and atherosclerosis in a mammalian subject comprising administering the composition of claim 1 to the mammalian subject in an amount effective for treating at least one of hyperlipidemia, fatty liver, steatohepatitis, obesity, hyperglycemia, metabolic syndrome, cardiovascular disease and atherosclerosis in the mammalian subject.

9. The method of claim 8, wherein the isolated peptide or polypeptide binds to importin beta in the mammalian subject.

10. The method of claim 8, wherein the composition further comprises an additional therapeutic agent.

11. The method of claim 10, wherein the additional therapeutic agent is an inhibitor of cholesterol synthesis.

12. The method of claim 11, wherein the inhibitor of cholesterol synthesis is a statin.

13. The method of claim 10, wherein the additional therapeutic agent is an inhibitor of cholesterol uptake.

14. The method of claim 8, wherein administration of the composition reduces inflammation in the mammalian subject.

15. The method of claim 8, wherein administration of the composition results in improved liver function in the mammalian subject.

16. The method of claim 8, wherein administration of the composition results in at least one of: reduced accumulation of cholesterol and triglycerides, a reduction in body weight and normalization of elevated blood glucose levels in the mammalian subject.

17. The method of claim 8, wherein the subject has atherosclerosis, and administration of the composition results in a reduction of at least one atherosclerotic lesion and reduces vascular inflammation associated with atherosclerosis in the subject.

18. The method of claim 8, wherein the subject has atherosclerosis.

* * * * *

SEQUENCE LISTING

```
<160> NUMBER OF SEQ ID NOS: 10

<210> SEQ ID NO 1
<211> LENGTH: 26
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 1

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 2
<211> LENGTH: 29
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 2

Ala Ala Val Ala Leu Leu Pro Ala Val Leu Leu Ala Leu Leu Ala Pro
```

```
                1               5                  10                 15
Cys Tyr Val Gln Arg Lys Arg Gln Lys Leu Met Pro Cys
                20                  25

<210> SEQ ID NO 3
<211> LENGTH: 28
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 3

Ala Ala Val Ala Leu Leu Pro Ala Val Leu Leu Ala Leu Leu Ala Pro
1               5                   10                  15

Cys Val Gln Arg Lys Arg Gln Lys Leu Met Pro Cys
                20                  25

<210> SEQ ID NO 4
<211> LENGTH: 28
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 4

Ala Ala Val Ala Leu Leu Pro Ala Val Leu Leu Ala Leu Leu Ala Pro
1               5                   10                  15

Cys Val Gln Arg Asp Glu Gln Lys Leu Met Pro Cys
                20                  25

<210> SEQ ID NO 5
<211> LENGTH: 16
<212> TYPE: PRT
<213> ORGANISM: HOMO SAPIENS

<400> SEQUENCE: 5

Ala Ala Val Ala Leu Leu Pro Ala Val Leu Leu Ala Leu Leu Ala Pro
1               5                   10                  15

<210> SEQ ID NO 6
<211> LENGTH: 10
<212> TYPE: PRT
<213> ORGANISM: HOMO SAPIENS

<400> SEQUENCE: 6

Val Gln Arg Lys Arg Gln Lys Leu Met Pro
1               5                   10

<210> SEQ ID NO 7
<211> LENGTH: 12
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 7

Cys Val Gln Arg Lys Arg Gln Lys Leu Met Pro Cys
1               5                   10

<210> SEQ ID NO 8
<211> LENGTH: 12
<212> TYPE: PRT
<213> ORGANISM: ARTIFICIAL SEQUENCE
<220> FEATURE:
<223> OTHER INFORMATION: SYNTHETIC CONSTRUCT
```

```
<400> SEQUENCE: 8

Cys Val Gln Arg Asp Glu Gln Lys Leu Met Pro Cys
1               5                   10

<210> SEQ ID NO 9
<211> LENGTH: 7
<212> TYPE: PRT
<213> ORGANISM: HOMO SAPIENS

<400> SEQUENCE: 9

Ala Ala Val Ala Leu Leu Pro
1               5

<210> SEQ ID NO 10
<211> LENGTH: 9
<212> TYPE: PRT
<213> ORGANISM: HOMO SAPIENS

<400> SEQUENCE: 10

Ala Val Leu Leu Ala Leu Leu Ala Pro
1               5
```